(12) United States Patent
Oaks et al.

(10) Patent No.: US 7,780,966 B2
(45) Date of Patent: Aug. 24, 2010

(54) ARTIFICIAL INVAPLEX

(75) Inventors: Edwin V. Oaks, Gambrills, MD (US); Kevin R. Turbyfill, Odenton, MD (US); Robert W. Kaminski, Germantown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 371 days.

(21) Appl. No.: 11/727,486

(22) Filed: Mar. 27, 2007

(65) Prior Publication Data

US 2008/0241196 A1    Oct. 2, 2008

(51) Int. Cl.
*A61K 39/116* (2006.01)

(52) U.S. Cl. .............. 424/203.1; 424/234.1; 424/257.1; 424/258.1; 424/193.1

(58) Field of Classification Search ........................ None
See application file for complete search history.

(56) References Cited

U.S. PATENT DOCUMENTS

| | | |
|---|---|---|
| 6,277,379 B1 | 8/2001 | Oaks et al. |
| 6,680,374 B2 | 1/2004 | Oaks et al. |

OTHER PUBLICATIONS

U.S. Appl. No. 60/524,639, filed Nov. 25, 2003, Oaks, et al.
"Development and evaluation of a *Shigella flexneri* 2a and *S. sonnei* bivalent invasion complex (Invaplex) vaccine," Oaks, et al., *Vaccine*, vol. 24, pp. 2290-2301 (2006).
"Isolation and Characterization of a *Shigella flexneri* Invasion Complex Subunit Vaccine," Turbyfill, et al., *Infection and Immunity*, vol. 68, No. 12, pp. 6624-6632 (Dec. 2000).
"Mucosal Adjuvant Properties of the *Shigella* Invasin Complex," Kaminski, et al., *Infection and Immunity*, vol. 74, No. 5, pp. 2856-2866 (May 2006).
"Cloning, Expression, and Affinity Purification of Recombinant *Shigella flexneri* Invasion Plasmid Antigens IpaB and IpaC," Picking, et al., *Protein Expression and Purification*, vol. 8, pp. 401-408 (1996).
"Evaluation of *Shigella* vaccine safety and efficacy in an intranasally challenged mouse model," Mallett, et al., *Vaccine*, vol. 11, pp. 190-196 (1993).
"*Shigella flexneri* Invasion Plasmid Antigens B and C: Epitope Location and Characterization with Monoclonal Antibodies," Mills, et al., *Infection and Immunity*, vol. 56, No. 11, pp. 2933-2941 (Nov. 1998).
"Characterization of invasion plasmid antigen genes (*ipaBCD*) from *Shigella flexneri*," Venkatesan, et al., *Proc. Natl. Acad. Sci. USA*, vol. 85, pp. 9317-9321 (Dec. 1988).
"Structural Characterization of the N Terminus of IpaC from *Shigella flexneri*," Harrington, et al., *Infection and Immunity*, vol. 71, No. 3, pp. 1255-1264 (Mar. 2003).
"The secreted IpaB and IpaC invasions and their cytoplasmic chaperone IpgC are required for intercellular dissemination of *Shigella flexneri*," Page, et al., *Cellular Microbioloty*, vol. 1, No. 2, pp. 183-193 (1999).
"Plaque Formation by Virulent *Shigella flexneri*," Oaks, et al., *Infection and Immunity*, vol. 48, No. 1, pp. 124-129 (Apr. 1985).
"Shigella Infection of Henle Intestinal Epithelial Cells: Role of the Host Cell," Hale, et al., *Infection and Immunity*, vol. 24, No. 3, pp. 887-894 (Jun. 1979).
"Shigella Infection of Henle Intestinal Epithelial Cells: Role of the Bacterium," Hale, et al., *Infection and Immunity*, vol. 24, No. 3, pp. 879-886 (Jun. 1979).
"Protein-protein interactions in the assembly of *Shigella flexneri* invasion plasmid antigens IpaB and IpaC into protein complexes," Davis et al., *Biochimica et Biophysica Acta*, vol. 1429, pp. 45-56 (1998).

*Primary Examiner*—Jennifer E Graser
(74) *Attorney, Agent, or Firm*—Elizabeth Arwine

(57) ABSTRACT

An artificial invasin complex is prepared from purified or recombinantly prepared invasins and gram negative bacteria lipopolysaccharides. Typically, IpaB is mixed with IpaC to form a IpaB:IpaC complex. This invasin protein complex is then mixed with the lipopolysaccharide to form an artificial invasin complex. Additional bioactive molecules can be incorporated into the complex during manufacture. This artificial invasin complex is similar in function to native Invaplex 24 or Invaplex 50. The artificial invasin complex has superior immunogenicity properties relative to the native complex and can be tailor made. Its method of preparation lends itself to scale up. The artificial invasin complex can facilitate transport of biomolecules, therapeutics and antibiotics across cell membranes in a manner similar to native *Shigella* Invaplex.

23 Claims, 13 Drawing Sheets

Fig. 1 SDS-PAGE Analysis of purified IpaB, IpaC and LPS used to assemble Invaplex$_{AR}$.

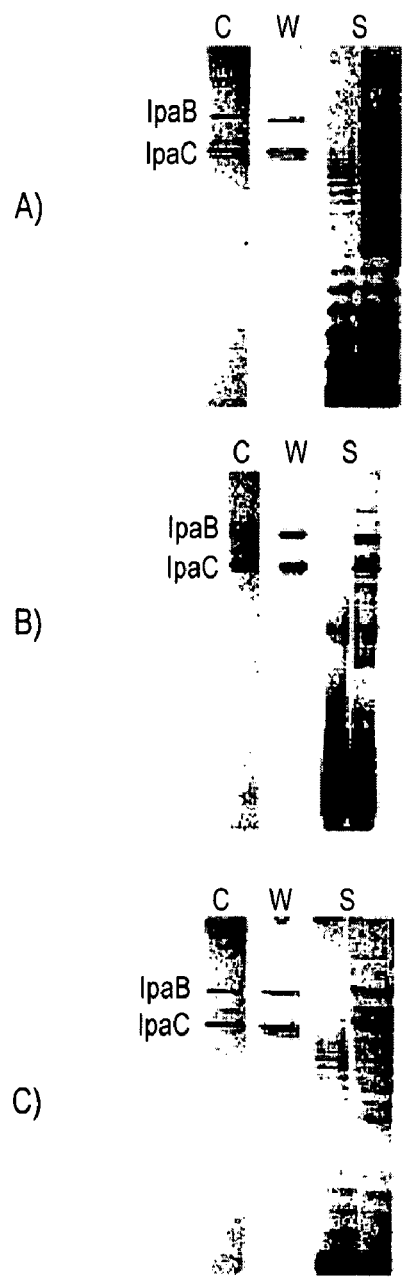
Fig. 2 Purification of S. flexneri 2a (panel A), S. sonnel (panel B) and S. dysenteriae 1 (panel C) Invaplex$_{AR}$ by anion exchange chromatography.

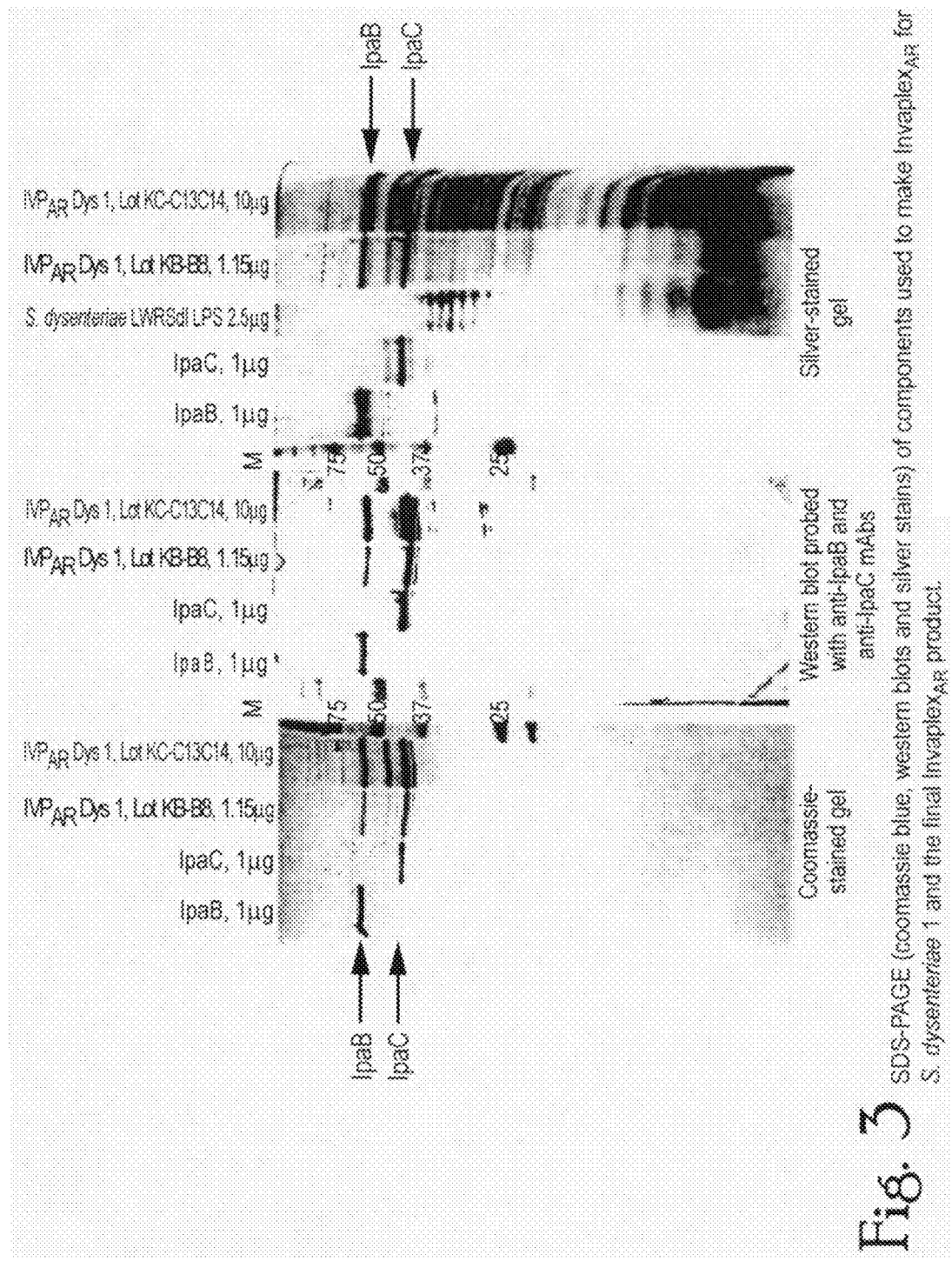

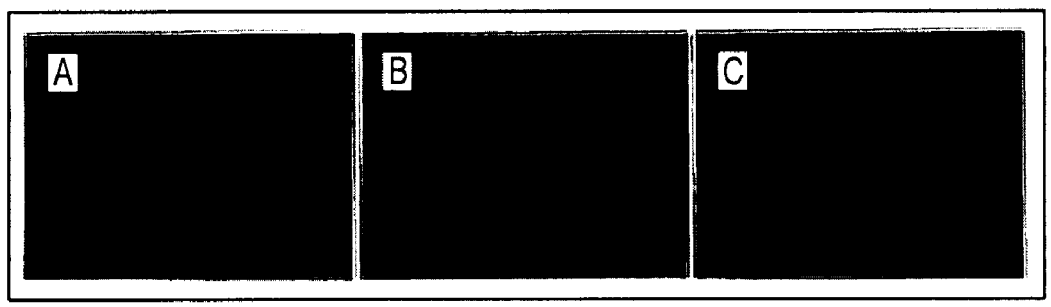
Fig. 4 Detection of internalized native and artificial *S. dysenteriae* 1 Invaplex in mammalian c

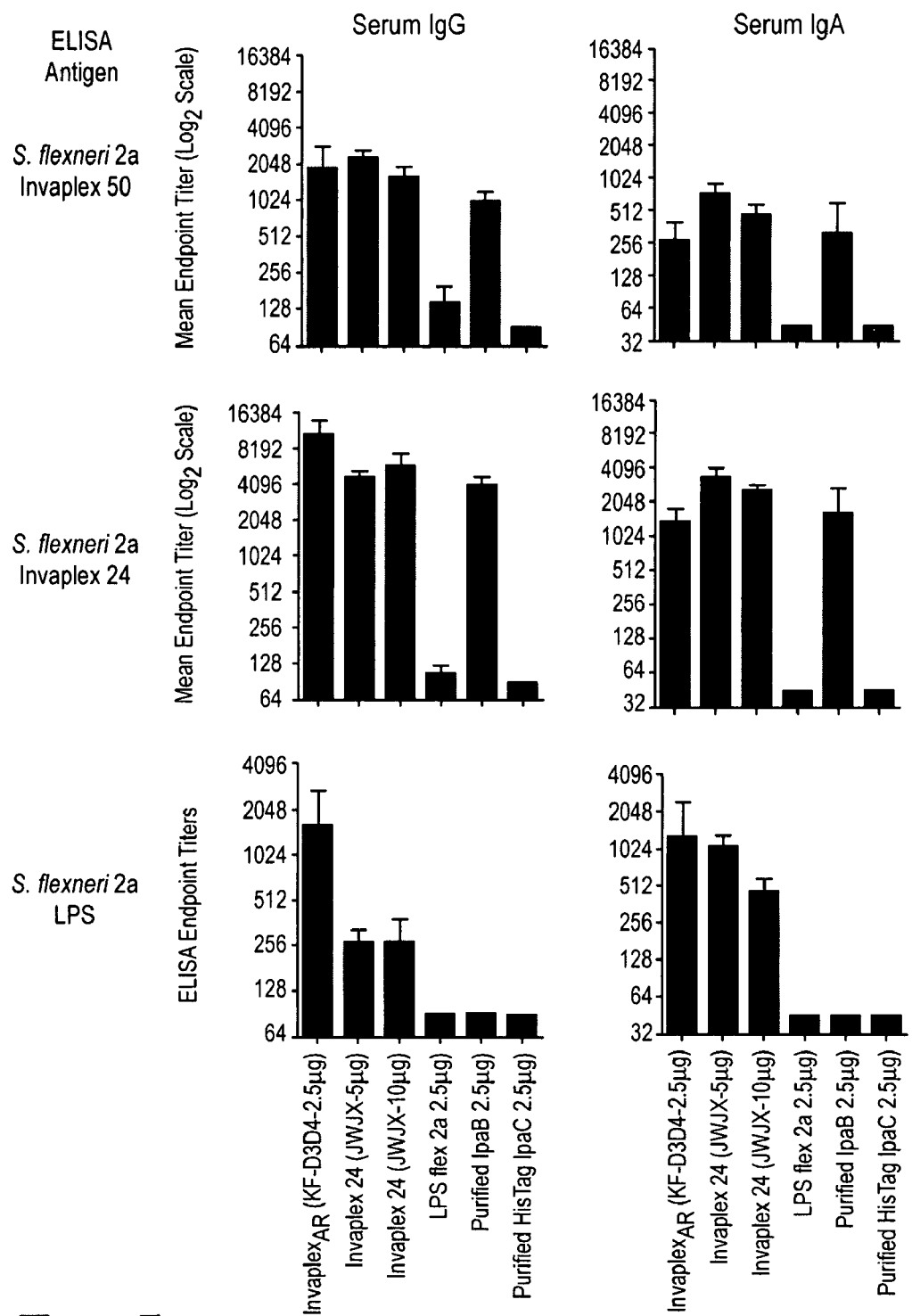
Fig. 5 Invaplex 50, Invaplex 24, and LPS-specific serum IgG and IgA endpoint titers on day 42 after intranasal immunization with S. flexneri 2a native Invaplex 24, Invaplex$_{AR}$, purified IpaB, IpaC, or S. flexneri 2a LPS.

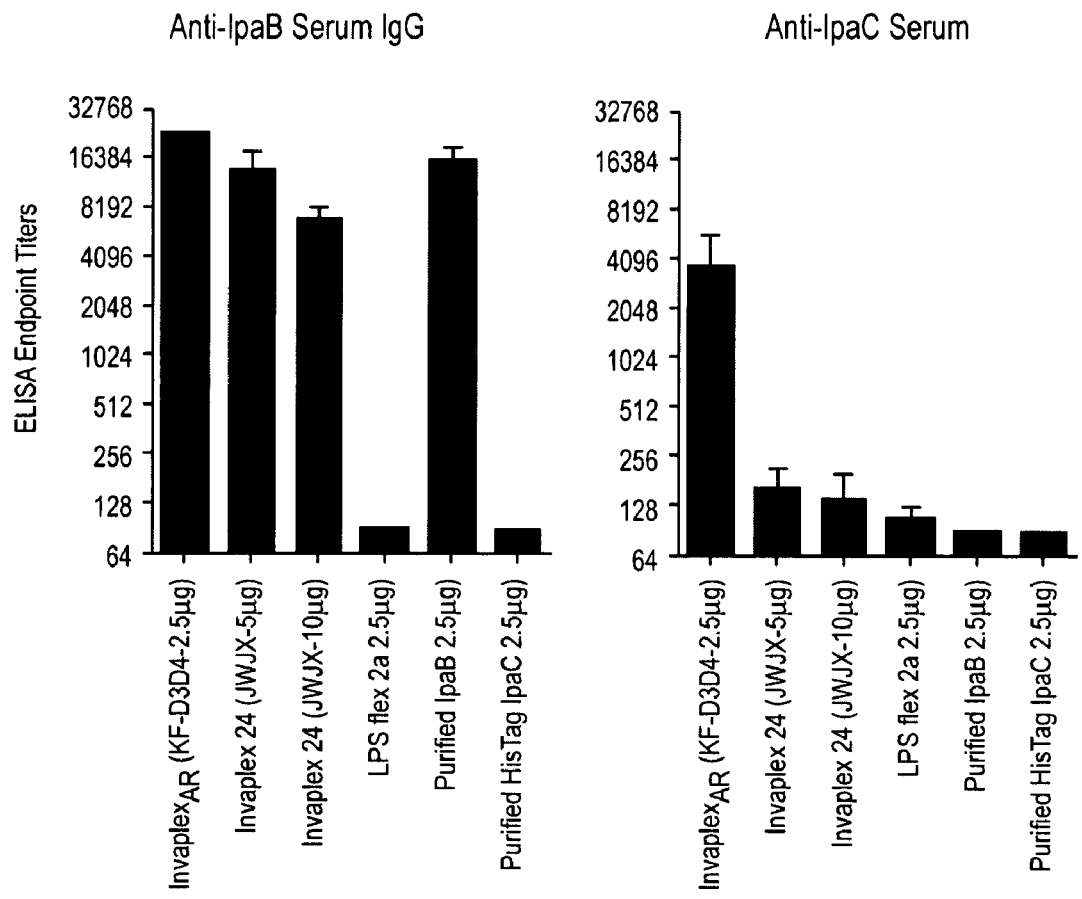
Fig. 6 Anti-IpaB and IpaC serum IgG endpoint titers on day 42 in mice intranasally immunized with *S. flexneri* 2a native Invaplex 24, Invaplex$_{AR}$, purified IpaB, IpaC, or *S. flexneri* 2a LPS.

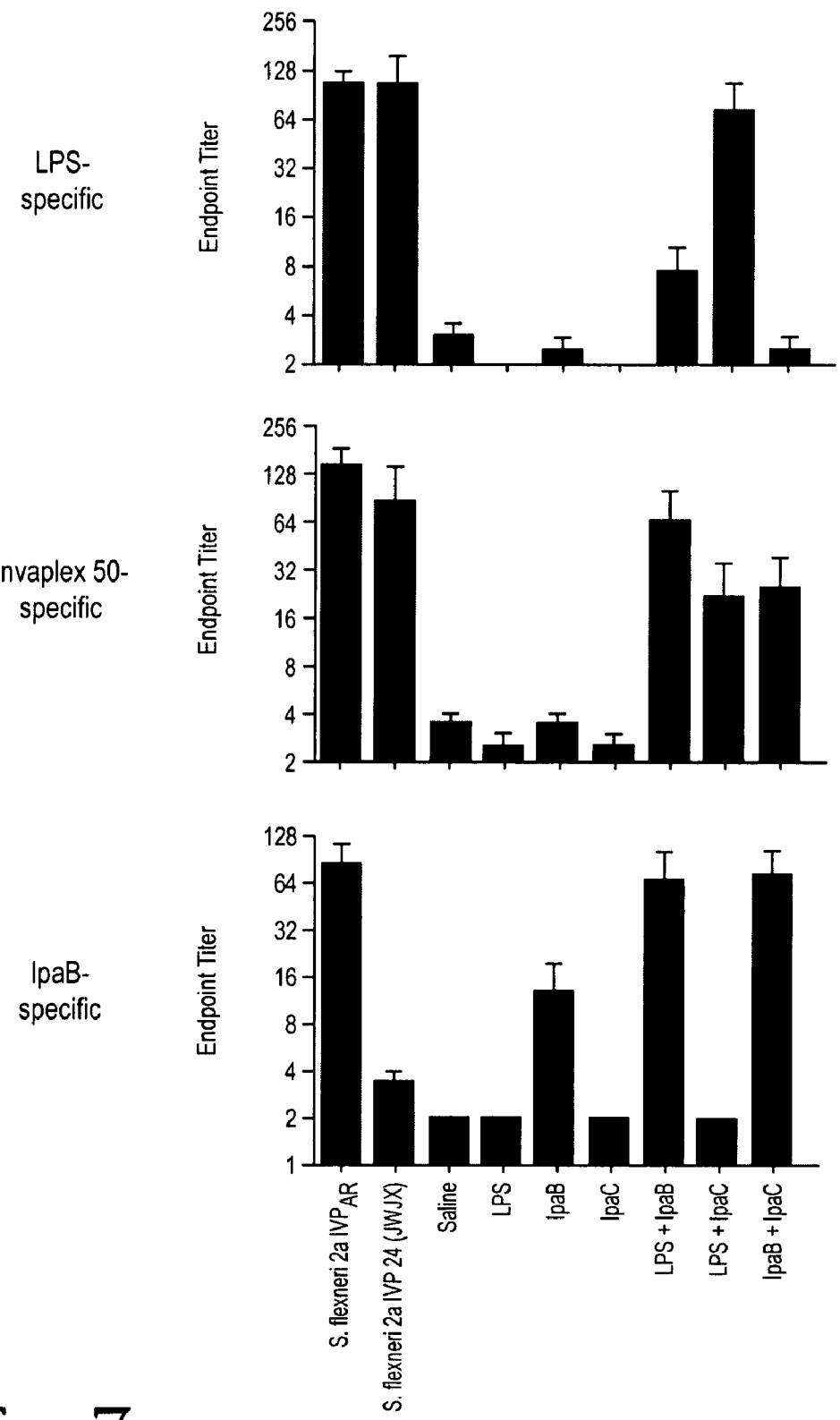
Fig. 7 Antigen-specific IgA in intestinal washes collected on day 35 from mice intranasally immunized with native *S. flexneri* 2a Invaplex or Invaplex$_{AR}$.

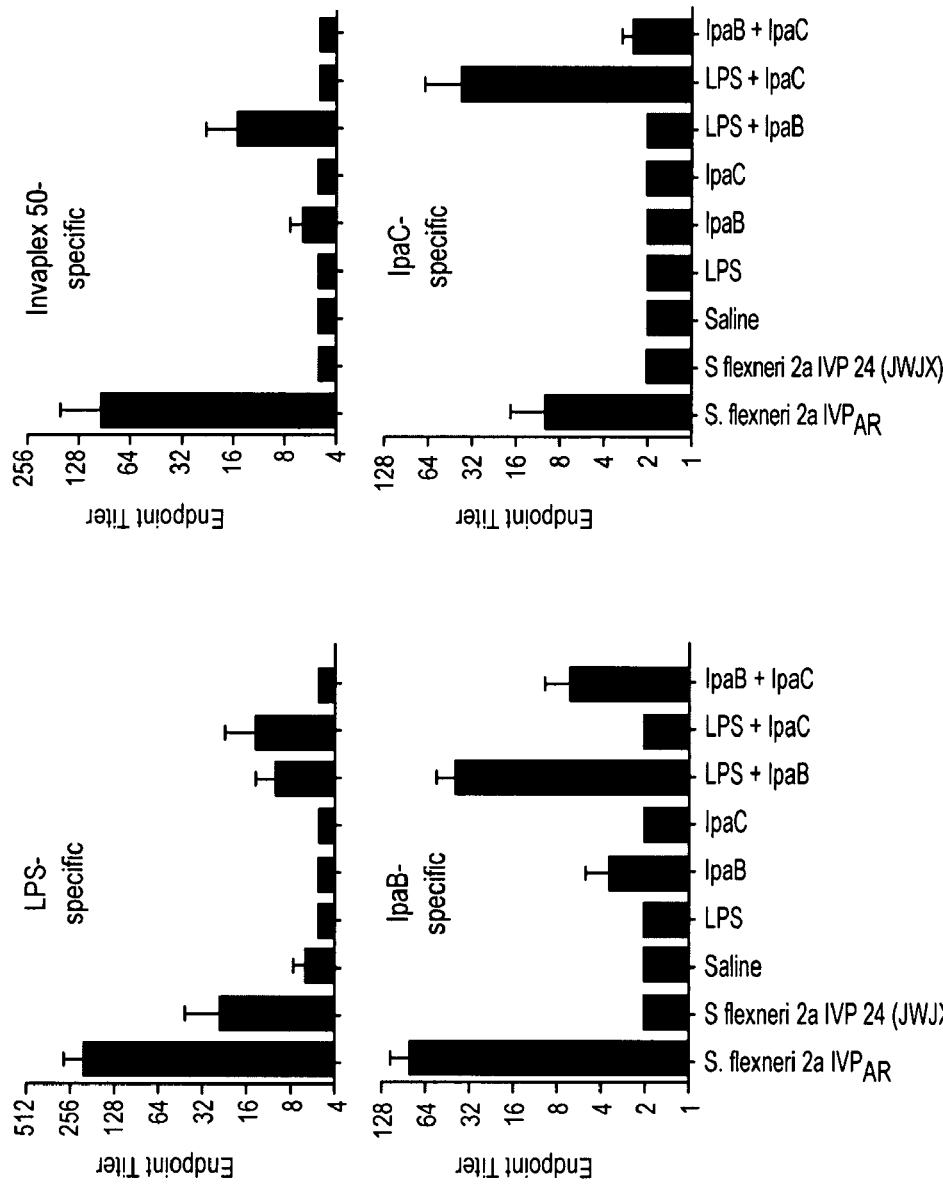
Fig. 8 Antigen-specific IgA in lung washes collected on day 35 from mice intranasally immunized with native S. flexneri 2a Invaplex or Invaplex$_{AR}$.

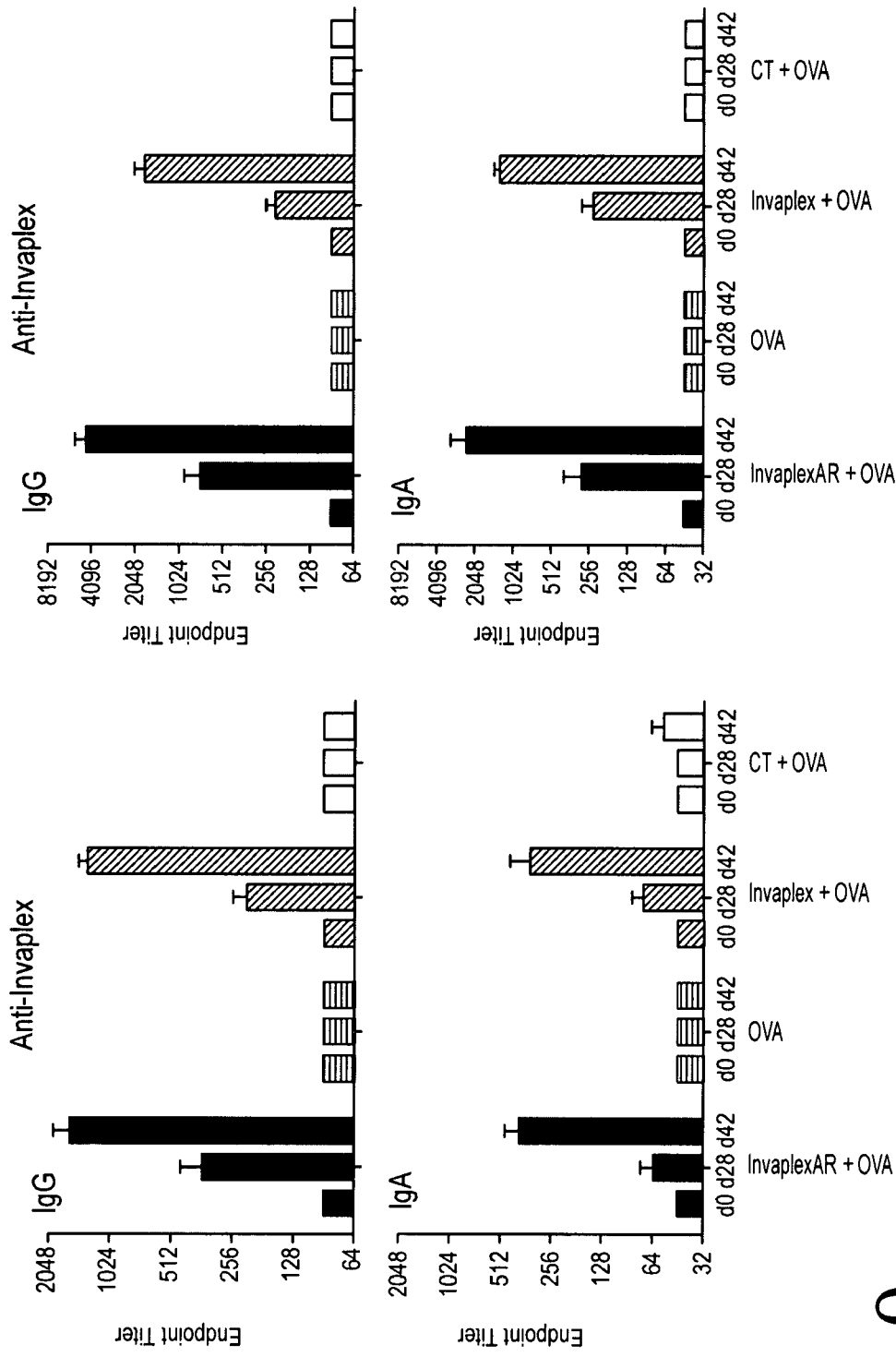
Fig. 9 Invaplex-specific serum IgG and IgA endpoint titers in mice after intranasal immunization with OVA alone, or OVA combined with Invaplex$_{AR}$, native Invaplex, or cholera toxin.

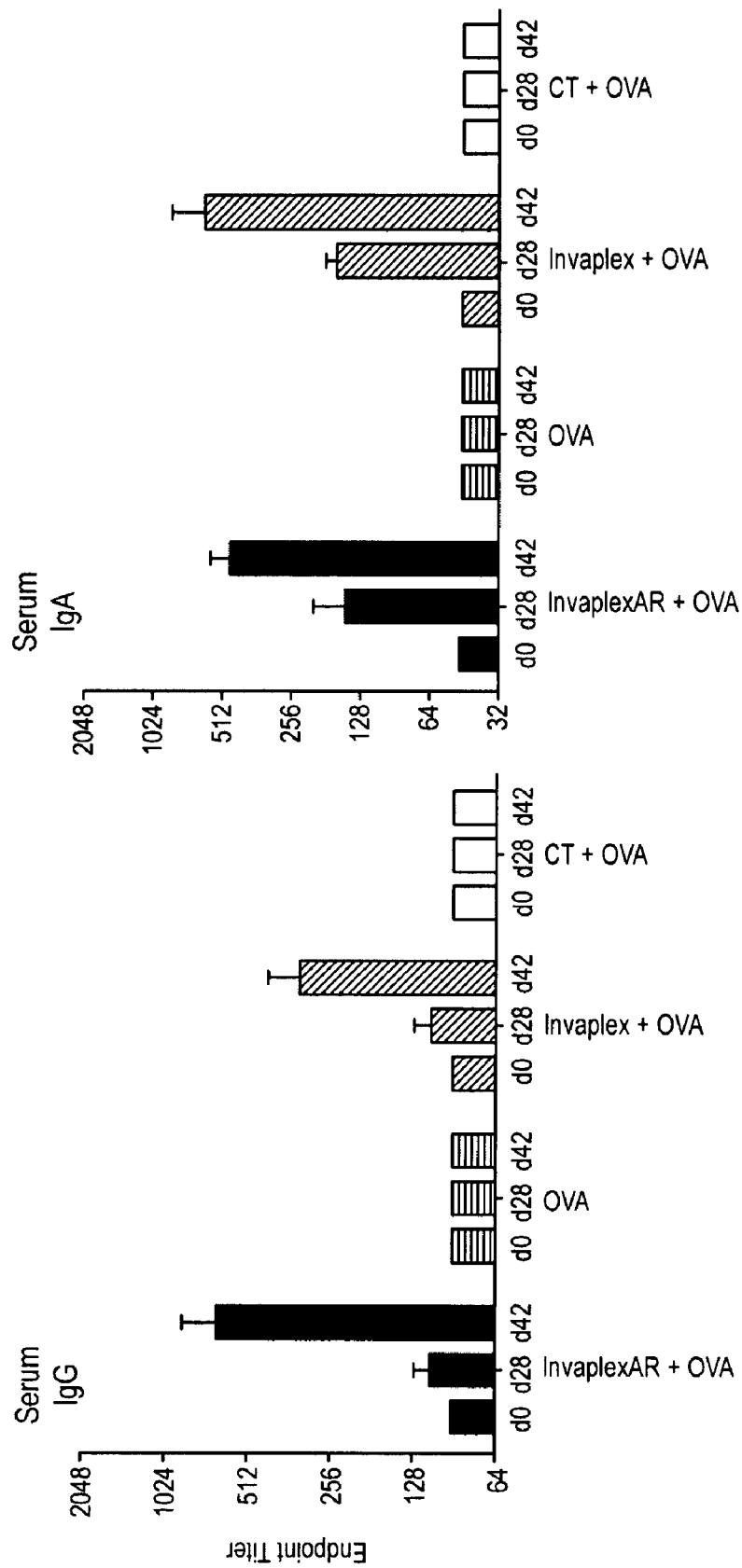
Fig. 10 *S. flexneri* 2a LPS-specific serum IgG and IgA endpoint titers in mice intranasally immunized with OVA alone, or OVA combined with Invaplex$_{AR}$, native Invaplex, or cholera toxin.

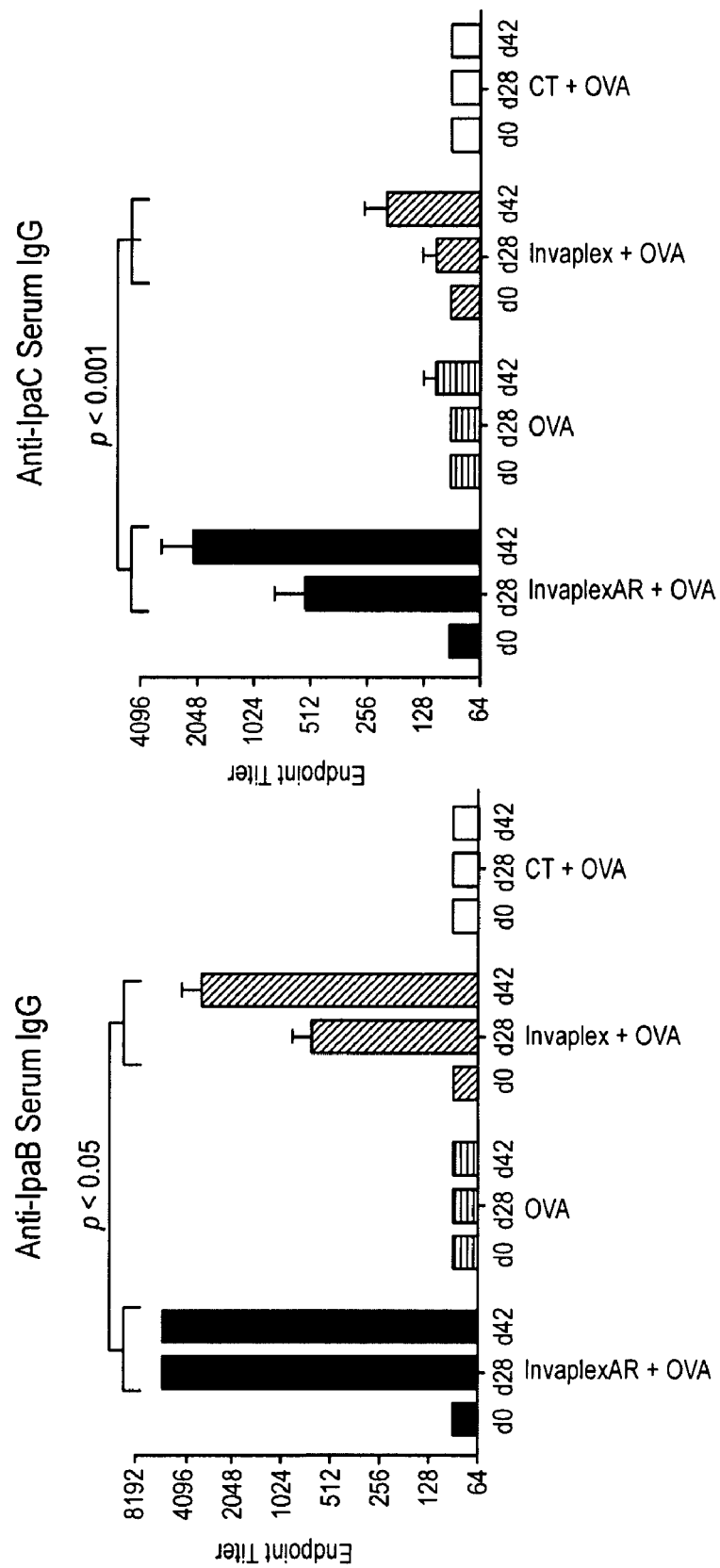
Fig. 11 *Shigella* invasin-specific serum IgG and IgA endpoint titers in mice intranasally immunized with OVA alone, or OVA combined with Invaplex$_{AR}$, native Invaplex, or cholera toxin.

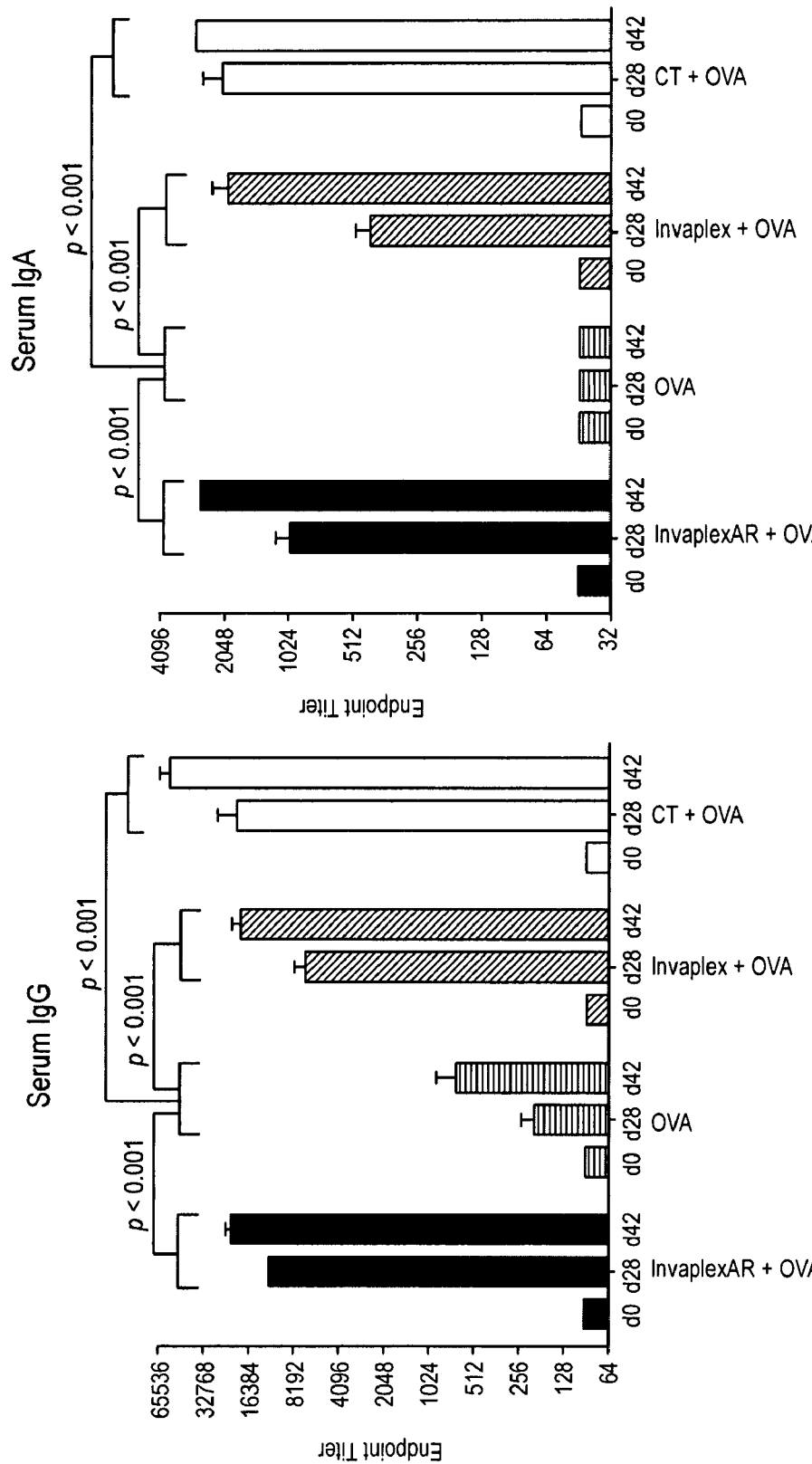
Fig. 12 Ovalbumin-specific serum IgG and IgA endpoint titers in mice intranasally immunized with OVA alone, or OVA combined with Invaplex$_{AR}$, native Invaplex, or cholera toxin.

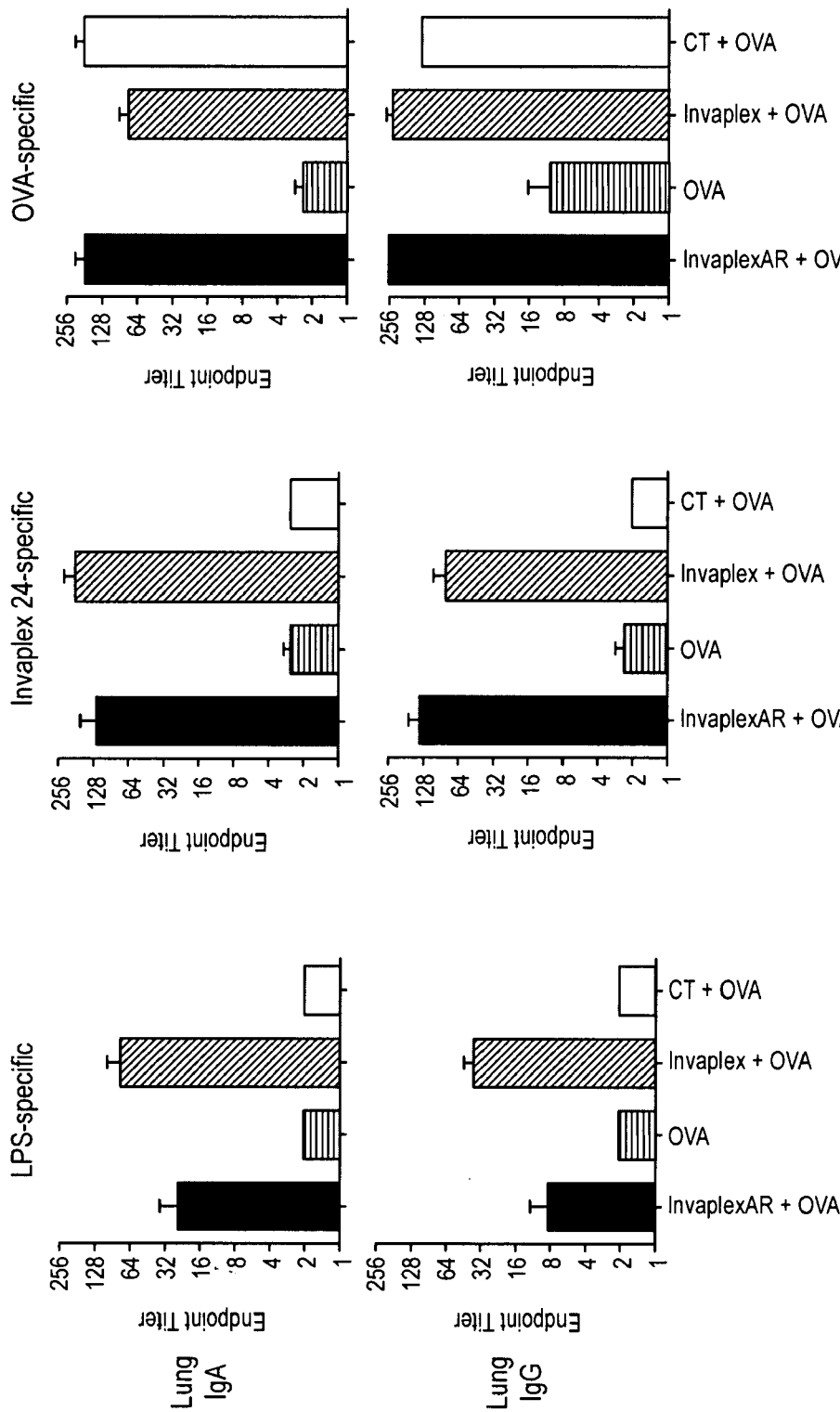
Fig. 13 S. flexneri 2a LPS, Invaplex 24 and ovalbumin-specific lung IgG and IgA endpoint titers in mice intranasally immunized with OVA alone, or OVA combined with InvaplexAR, native Invaplex, or cholera toxin.

ARTIFICIAL INVAPLEX

BACKGROUND OF THE INVENTION

1. Field of Invention

This invention provides a novel method for preparing an artificial Invaplex, an artificial invasin complex comprising at least two invasin proteins and a lipopolysaccharide from invasive gram negative bacteria. The artificial invasin complex of the present invention can be used as a vaccine, an adjuvant for vaccines, biochemical, or other substances, and as a diagnostic tool.

2. Description of Related Art

Shigellosis is a leading cause of human diarrheal disease particularly in developing countries where it is estimated that over 163 million cases, with 1 million fatal cases, occur annually [1]. The most common *Shigella* species causing disease worldwide are *S. flexneri* and *S. sonnei* [1]. A lower incidence (1.5 million cases/yr) of shigellosis in industrialized countries [1] implies that the adult population is non-immune and susceptible. Even in areas relatively free of shigellosis, massive destruction due to war or natural disasters, such as the earthquake of 1999 in Kocaeli, Turkey, can suddenly give rise to multispecies, multi-focal increases in dysentery [2]. Similarly, when deployed troops, relief workers, or travelers from industrialized countries are in areas endemic for *Shigella* or in areas where the local infrastructure has collapsed, the threat of exposure to multiple *Shigella* spp. may be significant. *S. dysenteriae* 1 causes the most severe form of shigellosis and is often associated with hemolytic uremic syndrome [3]. Although the incidence of *S. dysenteriae* 1 is not as high as that of *S. flexneri* or *S. sonnei*, epidemics caused by *S. dysenteriae* 1 often occurs every 10 to 12 years [4]. The periodic occurrence is probably due to many factors, one of which is the likely waning of immunity to *S. dysenteriae* 1. More important is the recent finding that antibiotic resistance to the flouroquinoline class of antibiotics has been demonstrated in *S. dysenteriae* 1 isolated in recent outbreaks [5, 6]. The likelihood of another epidemic of *S. dysenteriae* 1 is high and if it is caused by a strain with broad antibiotic resistance including the fluorquinolones, the consequences could be severe.

*Shigella* species are one of the few proven agents for biological terrorism. The extremely low infectious dose (for *S. dysenteriae* 1 it is reported to be 10 bacteria) [7] and the ease of growing the organism in simple bacteriological medium are suitable factors for considering *Shigella* spp as potent biological weapons. The proven effectiveness as a biological terrorism agent is a case in which employees in a hospital were deliberately infected with *S. dysenteriae* 2 by a disgruntled coworker who had "painted" muffins with the organism [8]. Other food-borne outbreaks of *Shigella* infections are well documented—from cold food on airlines to salads on cruise ships [9, 10] demonstrating the ease by which shigellae can cause disease in a susceptible population. Prevention of *Shigella* infections is best accomplished by environmental controls to include good sanitation and clean water supplies. Such infrastructure improvements are easily overcome if shigellae are deliberately planted in food or drinks. Furthermore, the ease of isolating shigellae from nature [5] and the simplicity of developing antibiotic resistant *S. dysenteriae* 1 strains in the laboratory validates this agent as a potential major bioterrorism threat. Although an initial outbreak might be difficult to completely stop in a non-immune population, it is important to limit secondary spread. An effective means of prevention are vaccines which are effective against shigellae regardless of antibiotic resistance.

The pathogenesis of *Shigella* spp. is attributed to the organism's ability to invade, replicate intracellularly, and spread intercellularly within the colonic epithelium. The initial entry of shigellae occurs through specialized intestinal epithelial cells called M cells. Several highly conserved, virulence plasmid-encoded proteins, called the invasion plasmid antigens (IpaA, IpaB, IpaC, and IpaD), are essential participants in the invasion process and are likely key to the efficiency of *Shigella* infections. Upon contact or attachment to host cells, the *Shigella* invasins are released [11] by a type III secretion apparatus [12] and induce a phagocytic event resulting in engulfment and internalization of the bacterium by the host cell [13]. The active components include an IpaB:IpaC complex that integrates into the host cell membrane, forming a channel by which other *Shigella* proteins gain entry into the host cell [14]. Recently, we have isolated from intact, virulent *Shigella* cells, an invasin protein-LPS complex which serves as an effective vaccine and adjuvant [15-19]. The *Shigella* invasin complex (Invaplex) is prepared by extracting intact virulent shigellae with water followed by anion-exchange chromatography of the water extract. Two fractions, called Invaplex 24 and Invaplex 50, contain the major antigens including LPS, IpaB and IpaC. The invasin complex (Invaplex) binds to surfaces of cultured epithelial cells whereas similar preparations from non-invasive shigellae do not exhibit this property. Shortly after attachment the Invaplex becomes localized inside the host cell via an acting-dependent endocytic event likely induced by the Invaplex. It appears that IpaC and IpaB have a significant role in the attachment and internalization process in that antibodies against IpaC or IpaB inhibit the binding of Invaplex to host cell membranes [20]. Antibodies to LPS do not alter the uptake event. Once internalized the Invaplex traffics through early endosomes, late endosomes, then the Golgi apparatus and eventually ends up free in the host-cell cytoplasm. The ability to bind to a eukaryotic host cell surface and stimulate endocytosis indicates that the Invaplex maintains an active, native virulence structure similar to that found in invasive *Shigella.*

Historically, successful *Shigella* vaccines have emphasized presentation of LPS in an effective manner to elicit protection. Many approaches have been used for *Shigella* vaccines including live attenuated vaccines [21, 22], killed whole cell vaccines [23, 24], and delivery of *Shigella* LPS or O-polysaccharides with carriers such as proteosomes [25], tetanus toxoid [26], ribosomes [27] or Invaplex (17, 18; see below). Only the live attenuated vaccines utilize the native invasiveness of the shigellae to deliver the LPS and protein antigens to the mucosal immune system presumably via the follicle-associated epithelium [14]. The residual pathogenicity of the attenuated vaccine strains may limit this approach unless further attenuation is achieved [28].

The ability to isolate a putative native surface structure such as Invaplex, which exhibits activities and immunogenicity similar to invasive shigellae, has significant implications in vaccine design and development. First, the isolated native complex may enhance delivery to the appropriate portal of entry (M-cells), similar to that targeted by live-attenuated vaccine strains. The attachment of Invaplex to host cells (and likely intestinal M cells or M-like cells in other mucosal tissues) allows the use of relatively low doses of this subcellular complex for immunization due to its delivery efficiency. Similar to live, attenuated vaccines Invaplex contains all major *Shigella* antigens (including IpaB, IpaC and LPS) and has the potential to stimulate an immune response equivalent to that produced during natural infection, including recognition of epitopes found only in native structures. Such epitopes may not be present in vaccines delivering only LPS or O-polysaccharide as the antigen. Furthermore, the conserved sequences and immunologic cross-reactivity of the Ipa proteins found in all *Shigella* species may enable a vaccine containing the invasins (or other conserved antigens) to be effective against more than one *Shigella* species.

The *Shigella* invasin complex (Invaplex) vaccine prepared from *Shigella flexneri* contains the major antigens LPS, IpaB and IpaC and is protective against homologous challenge in the guinea pig keratoconjunctivitis and mouse lung challenge models [17, 18]. After immunization, antibodies to LPS, IpaB and IpaC are produced which is similar to the antibody specificity observed after natural infection in humans [29]. Additional studies have shown that similar effective Invaplex vaccine products can be isolated from all species of *Shigella* and EIEC [15]. Although the Invaplex 24 and 50 preparations consist of many different proteins, the immunodominant antigens for Invaplex 24 are LPS, IpaB and IpaC and for Invaplex 50 the key antigens are LPS, IpaB, IpaC and the 84 kKa (EF-G) and 72 kKa (DnaK) protein antigens [18]. Other proteins within the Invaplex preparations are not immunogenic as determined by western blotting techniques using sera collected from Invaplex-immunized animals. Invaplex 24 and Invaplex 50 can be isolated from all wild-type *Shigella* species although often-times the Invaplex 24 form consistently contains higher quantities of IpaB, IpaC and LPS and fewer non-immunogenic proteins. With the Invaplex vaccine, the highest titers are often against the immunizing Invaplex (Invaplex 24 or Invaplex 50) when used as an ELISA antigen. This is thought to reflect a composite response to the Ipa proteins and LPS and to a set of conformational epitopes preserved by the invasin complex product when used as an ELISA antigen.

Efforts to identify and purify the active moiety within native Invaplex has identified a high molecular mass complex that was isolated by size exclusion chromatography from native Invaplex 24 preparations. This high molecular mass complex, referred to as "highly-purified" or HP Invaplex 24 consists of predominantly IpaB, IpaC and LPS. HP Invaplex 24 is immunogenic and protective at levels that are comparable to or exceed those exhibited by native Invaplex. No other fraction obtained by size-exclusion chromatography exhibited immunogenic or protective capacities comparable to native Invaplex and for this reason the HP Invaplex 24 was considered to be the active moiety within native Invaplex responsible for its immunogenicity and efficacy as a vaccine.

Virulent shigellae cause disease by invading, replicating, and spreading within the colonic epithelium by virtue of a complex series of cellular and molecular events orchestrated by an array of plasmid-encoded virulence factors among which are the Ipa proteins [49]. After invading the intestinal epithelial cells of the colonic mucosa a mucosal inflammatory response occurs characterized by an increase in proinflammatory cytokines that leads to recruitment of neutrophils and macrophages/monocytes. The resulting disease, shigellosis or bacillary dysentery, causes mild to severe diarrhea, fever and intestinal lesions. Since testing of the efficacy of vaccines in humans and nonhuman primates involves a post-immunization challenge with virulent shigellae, the use of small animal models for initial testing of vaccine candidates reduces the risk of illness to the human volunteers and primates. Small animal models such as the guinea pig keratoconjunctivitis model or the mouse lung model of experimental infection with shigellae are largely used in studies of pathogenesis and preclinical vaccine evaluation [18, 44, 50] with the mouse model often used in initial evaluations and the guinea pig model for testing vaccines that are protective in the mouse model.

The mouse intranasal challenge model of *Shigella* infection is useful to evaluate *Shigella* vaccines [18, 31, 51, 52]. The pathogenesis and immunobiology observed in the pulmonary model parallel those seen in the colon; that is, virulent *Shigella* strains invade, replicate, and spread within the epithelium and subsequently elicit antibody as well as cytokine responses [52]. After infection the mice lose weight and ultimately die unless protective immunity is present. The ability to measure a secretory antibody response, the cellular immune responses, and cytokine responses (largely due to the availability of commercial reagents) makes the mouse model highly attractive for studies on the immunobiology of shigellosis.

The guinea pig model is an accepted model that is useful for studying the virulence of both wild-type and attenuated *Shigella* strains, and for evaluating the efficacy of potential vaccine candidates [18, 44, 45, 53-56]. Several routes of immunization can be employed for immunization depending upon the vaccine: oral, intranasal, ocular, and parenteral immunizations have all been used to protect against ocular challenge. Immunogenicity and efficacy of *Shigella* vaccine in the guinea pig keratoconjunctivitis model is now used as a stepping-stone to phase 1 clinical studies.

There exists a need for a chemically defined, artificial Invaplex moiety, which is similar or superior in biological activity to a native Invaplex. There is also a need for an Invaplex manufacturing process which can be readily scaled up and results in a more specifically defined product dependent on the ratios of the individual component parts used. There is also a need for an Artificial Invaplex which is capable of being designed for specific applications or customized functionality. There is also a need for an Invaplex vaccine that can be manufactured quickly from its component parts which can be stockpiled in anticipation of future vaccine needs.

BRIEF SUMMARY OF THE INVENTION

The invention relates to an artificial Invaplex and a method for its manufacture. The artificial Invaplexes (InvaplexAR) are similar in composition to HP Invaplex 24. HP Invaplex 24 contains IpaB, IpaC and lipopolysaccharride. The Artificial Invaplex functions as an Invaplex obtained from a native source, though it may have superior activity. The Artificial Invaplex has defined components: a complex comprising the invasion proteins IpaB and IpaC, which complex is additionally complexed with a serotype-specific lipopolysaccharide component from a gram negative bacteria. The lipopolysaccharide is an immunogen as are IpaB and IpaC. InvaplexAR can function as a mucosal adjuvant and enhance both serum and mucosal antigen-specific antibody responses as well as cell-mediated immune responses. It is also possible to use other invasins from other bacteria species including SipB, SipC or viral (reo virus) proteins associated with endocytosis events or tissue tropisms.

The serotype associated lipopolysaccharides are obtained from gram negative bacteria such as *Shigella flexneri, Shigella sonnei, Shigella dysenteriae, Shigella boydii, enteroinvasive E. coli, Yersinia* or *Salmonella*. The more preferred species include *S. flexneri, S. sonnei, S. boydii, S. dysenteriae* or *enteroinvasive E. coli.*

In preparing Artificial Invaplex, e.g. Invaplex$_{AR}$, the invasin proteins used are either highly purified (hp-) or recombinantly (r-) prepared IpaB and IpaC and purified lipopolysaccharide are used as starting materials. The IpaB and IpaC proteins are mixed to form IpaB:IpaC complex. This complex is mixed with at least one lipopolysaccharide associated with a serotype of a gram negative bacteria to form an Artificial Invaplex. The artificial Invaplex is recovered from the mixture. Typically, the Artificial Invaplex is removed based on its charge. Other purification techniques can be used. The order of addition can be varied. The lipopolysaccharide can be complexed with either of the invasin proteins and then with the other invasin protein to form the Artificial Invaplex.

Typically, the amount of IpaC presented relative to IpaB present falls within a ratio range of 0.08:1 to 80:1, preferably 0.8:1 to 20:1, more preferably at least 8:1. It is even more preferred for the amount of IpaC in the first mixing step to be present in at least a ten fold excess relative to IpaB. In the second mixing step, the lipopolysaccharide and protein (IpaB and IpaC) are present at a ratio within the range 0.01:1 to 10:1, preferably at least 1:2. It is possible in the second mixing step to include two or more types of lipopolysacchides, which results in an artificial Invaplex being suitable for use in multivalent immunogenic compositions, as vaccines. It is also possible in addition to the lipopolysaccharide to include a detectant label, antibiotic, therapeutic or biomolecule comprising an enzyme, protein, polysaccharide, RNA or DNA, or derivatives thereof which one wants to incorporate within a cell. This gives rise to possible therapeutic and analytical/diagnostic uses.

The artificial Invaplexes of the invention include those where the IpaC and IpaB are present in a ratio selected from 0.08:1 to 80:1, preferably, 0.8:1 to 20:1, even more preferred approximately 8:1 and the lipopolysaccharride (LPS) is present at a ratio selected from the range of 0.01:1 to 10:1, preferably, from 0.5:1 to 5:1, even more preferred approximately 0.5:1 relative to the total protein (IpaB and IpaC) present. The preferred artificial Invaplexes include *S. flexneri* Invaplex$_{AR}$, *S. dysenteriae* Invaplex$_{AR}$ or *S. sonnei* Invaplex$_{AR}$ The artificial Invaplexes of the invention can be formulated to form compositions suitable for use as immunogenic compositions or vaccines. The Invaplex can be used as the immunogen and/or as the adjuvant. The compositions would include in addition to the artificial Invaplex at least a pharmaceutically acceptable carrier. The amount of Invaplex present is an amount effective for the desired function and in at least the first instance, is empirically determined. This amount is expected to be similar to that of a native Invaplex, e.g. Invaplex 24, used for a similar function.

In addition the artificial invasin complexes facilitate the transport of a molecule and related materials across cell membranes. These molecules can be in close proximity to a cell of interest and the artificial Invaplex or can be present within and/or on the artificial Invaplex. The molecules can be detectant labels, antibiotics, therapeutics, and biomolecules including proteins, enzymes, RNA, DNA, lipopolysaccharides, polysaccharides and the like.

The artificial Invaplexes can be used in methodologies where native Invaplexes have been used, e.g. methods of immunization, methods for facilitating the transport of biomolecules, e.g. DNA, RNA, proteins, across the membranes of cells, etc. The artificial Invaplex can be designed to be multivalent or to have superior activity relative to the native Invaplex. This should improve the performance of the existing method or its utility. Invaplex$_{AR}$ made from recombinant IpaB, IpaC and either *S. sonnei* LPS or *S. flexneri* 2a LPS induced immune responses that are comparable or higher in magnitude to the immune response induced with native Invaplex. IpaB and IpaC responses after immunization with Invaplex$_{AR}$ were consistently of higher magnitude than those induced after immunization with native Invaplex. Immunization with Invaplex$_{AR}$ offers comparable or higher levels of protection against challenge in the mouse and guinea pig models as compared to immunization with native Invaplex. Immunization with Invaplex$_{AR}$ induces cellular immunity which is of greater magnitude than the *Shigella*-specific response induced with native Invaplex. See, for example, Tables 7 and 8.

BRIEF DESCRIPTION OF THE DRAWINGS

FIG. 1 shows SDS-PAGE analysis of purified IpaB, IpaC and LPS used to assemble Invaplex$_{AR}$. Purified recombinant IpaB (left) and IpaC (center) were separated by SDS-PAGE and blotted to nitrocellulose (left panel for IpaB and IpaC) or stained with coomassie blue (right panel for IpaB and IpaC). Proteins blotted to nitrocellulose were probed overnight with the anti-IpaB mAb 2F1 or anti-IpaC mAb2G2. *S. dysenteriae* 1 LPS (right panel) was separated by SDS-PAGE.

FIG. 2 shows purification of *S. flexneri* 2a (panel A), *S. sonnei* (panel B) and *S. dysenteriae* 1 (Panel C) Invaplex$_{AR}$ Purified IpaB, IpaC, and LPS from *Shigella* species (as indicated) were mixed together at 37° C. for 2 hrs in the presence of 0.5 M NaCl. Purification: after incubation, the mixture was diluted 1/5 and then applied to a HiTrap™ Q HP column and resolved with a NaCl step gradient as previously described [17]. Fractions within each peak were analyzed by 13% SDS-PAGE. The Invaplex$_{AR}$ (red peak) eluted in the 0.5 M NaCl (50% Buffer B) step. Gels were either stained with Coomassie Blue (gel C), blotted to nitrocellulose and probed with mAbs specific for IpaB and IpaC (gel W) or reacted with silver (gel S). Purified LPS from the designated *Shigella* species is in the left lane of the "S" panel. The 0.5M NaCl step contained the majority of IpaB, IpaC and LPS; the 0.24 M NaCl peak contained small quantities of IpaB, IpaC and LPS.

FIG. 3 shows SDS-PAGE (coomassie blue, western blots and silver stains) of components used to make InvaplexAR for *S. dysenteriae* 1 and the final Invaplex$_{AR}$ product. The gel on the left is a coomassie blue stained gel of purified IpaB, IpaC and two different lots of *S. dysenteriae* 1 Invaplex$_{AR}$. The prominence of IpaB and IpaC are evident in the Invaplex$_{AR}$. The middle panel is a western blot that used mAbs to IpaB and IpaC to probe the purified proteins and the two different lots of *S. dysenteriae* 1 InvaplexAR. The panel on the right is a silver-stained gel of the purified IpaB and IpaC proteins, purified LPS, and two lots of *S. dysenteriae* 1 Invaplex$_{AR}$ which show both the Ipa protein bands and the LPS bands in the InvaplexAR.

FIG. 4 shows detection of Internalized native and artificial *S. dysenteriae* 1 Invaplex in mammalian cells. BHK-21 cells were incubated at 37° C. for 60 min with LPS (A), native Invaplex 24 (B), or Invaplex$_{AR}$ (C) all produced from *S. dysenteriae*-1. Fixed cells were probed with anti-S. dysenteriae 1 polyclonal sera followed by GAM-IgG-$OG_{488}$ to visualize internalized Invaplex (green). Cells were counterstained with DAPI to identify the nucleus (blue). *Shigella* LPS was not internalized by the host cells whereas both native Invaplex and artificial Invaplex were internalized by ~70% of cells.

FIG. 5 shows Invaplex 50, Invaplex 24 and LPS-specific serum IgG and IgA end point titers on day 42 after intranasal immunization with *S. flexneri* 2a native Invaplex 24, Invaplex$_{AR}$, purified IpaB, IpaC or *S. flexneri* 2a LPS.

FIG. 6 shows Anti-IpaB and IpaC serum IgG endpoint end point titers on day 24 after intranasal immunization with *S. flexneri* 2a native Invaplex 24, Invaplex$_{AR}$, purified IpaB, IpaC or *S. flexneri* 2a LPS.

FIG. 7 shows antigen-specific IgA in intestinal washes collected on day 35 from mice intranasally immunized with native *S. flexneri* 2a Invaplex or Invaplex$_{AR}$. Data represents the mean endpoint titer plus one standard error of the mean for each group of mice (n=4 mice/grp).

FIG. 8 shows antigen-specific IgA in lung washes collected on day 35 from mice intranasally immunized with native *S. flexneri* 2a Invaplex or Invaplex$_{AR}$. Data represents the mean endpoint titer plus one standard error of the mean for each group of mice (n=4 mice/grp).

FIG. 9 shows Invaplex-specific serum IgG and IgA endpoint titers in mice after intranasal immunization with OVA alone, or OVA combined with InvaplexAR, native Invaplex, or cholera toxin. Groups of mice were intranasally inoculated on day 0, 14, and 28 with OVA or OVA combined with either Invaplex$_{AR}$, Invaplex or CT. Blood collected on day 0, 28, and 42 were analyzed by ELISA for anti-Invaplex serum IgG and IgA endpoint titers. Data represents the mean (n=5 mice/grp) endpoint titer±1 SEM.

FIG. 10 shows *S. flexneri* 2a LPS-specific serum IgG and IgA endpoint titers in mice intranasally immunized with OVA alone, OVA combined with InvaplexAR, native Invaplex, or cholera toxin. Groups of mice were intranasally inoculated on day 0, 14, and 28 with OVA or OVA combined with either Invaplex$_{AR}$, Invaplex, or CT. Blood collected on day 0, 28, and 42 were analyzed by ELISA for anti-Invaplex serum IgG and IgA endpoint titers. Data represents the mean (n=5 mice/grp) endpoint titer±1 SEM.

FIG. 11 shows *Shigella* invasion-specific serum IgG and IgA endpoint titers in mice intranasally immunized with OVA alone, or OVA combined with InvaplexAR, native Invaplex or cholera toxin. Groups of mice were intranasally inoculated on day 0, 14, and 28 with OVA or OVA combined with either Invaplex$_{AR}$, Invaplex or CT. Blood collected on day 0, 28, and 42 were analyzed by ELISA for anti-IpaB and IpaC serum IgG endpoint titers. Data represents the mean (n=5 mice/grp) endpoint titer±1 SEM. Comparisons between groups were accomplished using two-way ANOVA analysis of natural log-transformed endpoint titers.

FIG. 12 shows ovalbumin-specific serum IgG and IgA endpoint titers in mice intranasally immunized with OVA alone, or OVA combined with InvaplexAR, native Invaplex or cholera toxin. Groups of mice were intranasally inoculated on day 0, 14, and 28 with OVA or OVA combined with either Invaplex$_{AR}$, Invaplex, or CT. Blood collected on day 0, 28, and 42 were analyzed by ELISA for anti-OVA serum IgG and IgA endpoint titers. Data represents the mean (n=5 mice/grp) endpoint titer±1 SEM. Comparisons between groups were accomplished using two-way ANOVA analysis of natural log-transformed endpoint titers.

FIG. 13 shows *S. flexneri* 2a LPS, Invaplex 24 and ovalbumin-specific lung IgG and IgA endpoint titers in mice intranasally immunized with OVA alone, or OVA combined with InvaplexAR, native Invaplex or cholera toxin. Groups of mice were intranasally immunized on day 0, 14, and 28 with OVA or OVA combined with either InvaplexAR, Invaplex, or CT. Lung washes were collected from individual mice on day 42 and analyzed by ELISA for anti-LPS, anti-Invaplex 24, and anti-OVA IgG and IgA endpoint titers. Data represents the mean (n=5 mice/grp) endpoint titer±1 SEM.

DETAILED DESCRIPTION OF THE INVENTION

Biochemistry of Artificial Invaplex Production and Purification of Recombinant IpaB and IpaC and native *S. flexneri, S. sonnei* and *S. dysenteriae* 1 LPS

Purification of Ipa Proteins

The Ipa proteins are highly conserved in all *Shigella* spp [32, 33]. Recombinant *E. coli* expressing either IpaB or IpaC have been previously described. Two strategies are available for purifying recombinant Ipa proteins. Histidine-tagged (HisTag) recombinant IpaC is purified by affinity chromatography using nickel columns. The effect of the histidine residues on the Ipa protein's biological or immunological function or the ability of the proteins to form Invaplex is not known but HisTag-IpaC appears to maintain biological activity [30]. An alternative purification procedure has been used to produce recombinant IpaB. This method takes advantage of IpaB's native affinity for the chaperone IpgC [34, 35]. By co-expressing IpaB together with the HisTag-chaperone IpgC in the same recombinant organism, it will be possible to purify the IpaB/chaperone complex. After purification, the HisTag-IpaC/IpaB protein complex is denatured resulting in monomeric IpaB protein and HisTag-IpgC which allows the HisTagged chaperone to be selectively removed on a nickel column while the free Ipa protein runs through the column.

Purification of HisTag-IpaC

The recombinant IpaC was expressed in an *E. coli* background using an IPTG inducible expression system (pET plasmid). Specifically, the IpaC gene was cloned into the pET15b plasmid (Novagen) and expressed in the *E. coli* vector BL21(DE3)pLysS [30]. The recombinant IpaC protein has several histidine residues on the amino terminal end that allows subsequent purification on a nickel column [30]. The IpaC protein expressed in the recombinant is located in inclusion bodies and requires solubilization with urea. Removing the urea often leads to insolubility if the IpaC concentration is too high (>1 mg/ml). Thus, IpaC eluted from the nickel column was maintained in urea to maintain solubility. Using small-scale cultures (3 L) it has been possible to produce approximately 75 mg of purified IpaC with a yield of approximately 8 mg/L. The product is greater than 90% pure and is reactive with anti-IpaC mAb 2G2 [32] (FIG. 1). The purified protein is soluble and can be stored frozen. An example of purified IpaC is in FIG. 1.

Purification of IpaB

The recombinant organism expressing IpaB is in an *E. coli* BL21(DE3) background. The IpgC gene was cloned into pET15b; the IpaB gene was cloned separately into the pACYC-duet vector. After IPTG induction the HisTag IpgC/IpaB complex is solubilized and purified on a nickel affinity column. The HisTag-IpgC/IpaB complex is released with EDTA and prepared for second application to the nickel affinity column by removal of the EDTA and the addition of the non-ionic detergent OPOE (N-octyl-oligo-oxyethylene) to a final concentration of 1% v/v. The OPOE will disrupt the HisTag-IpgC/IpaB complex thereby allowing the free HisTag-IpgC protein to bind to the nickel (Ni-Sepharose) column and the untagged, free IpaB to flow through the column for collection. Fractions from the void volume were probed for IpaB with anti IpaB mAb 2F1. Positive fractions were analyzed by SDS-PAGE (stained) to determine if contaminating HisTag-IpgC was present. If so, the material was treated again with OPOE and reapplied to the nickel column to remove residual HisTag-IpgC. The resultant soluble IpaB product has little to no HisTag-IpgC "contamination", is over 90% pure and reacts with anti IpaB mAb 2F1 [32] (FIG. 1). The yield of IpaB per liter of starting culture was approximately 3.5 mg/L.

Purification of S. flexneri 2a, S. sonnei, or S. dysenteriae 1 LPS

S. flexneri 2a, S. sonnei, and S. dysenteriae 1 LPS were produced by the Westphal procedure [36] which involves a hot phenol/water extraction of the shigellae. Virulent or attenuated strains of Shigella can be used as source of LPS as long as the smooth LPS phenotype is expressed. In experiments described below, wild-type S. flexneri 2a (strain 2457T) and S. sonnei (Mosely) were used. For S. dysenteriae 1, the attenuated strain WRSd1 was used to minimize risk of infection to laboratory personnel. WRSd1 is a virG, stx knockout previously produced at WRAIR [37].

Extraction, Purification and Characterization of LPS

LPS is extracted by the Westphal procedure [36]. Briefly, the bacterial cell pellets are suspended in hot (68° C.) distilled water (5 ml water for each gram of pellet). An equal amount of phenol, heated to 68° C., is added and the pellet solution is vigorously shaken for 15 minutes. The bottles are then cooled to approximately 10° C.±5° C. The samples are centrifuged, the aqueous phase removed and stored at 4° C. Extraction of the cell mass is performed a second time and all aqueous phases are pooled. The aqueous phase is dialyzed against distilled water for two days, and then centrifuged (8000×g, 30 min) to remove extraneous cellular debris. This supernatant is subjected to ultracentrifugation (90,000×g) for 2 hours and the pellet is saved. The pellet is rinsed with sterile distilled water, resuspended in sterile distilled water overnight at 4° C., pooled and lyophilized. The final lyophilized product is weighed and then a small portion (<10 mg) is removed, dissolved in 1 ml of endotoxin-free water and characterized biochemically (see below).

Endotoxin content of the purified LPS is performed by the chromogenic LAL. E. coli endotoxin serves as a control reagent for this analysis. All results are reported in terms of international endotoxin units (EU). The purified LPS is also analyzed by SDS-PAGE with silver stain to determine if the typical multiple band profile of smooth LPS are present. FIG. 1 shows a silver stained gel of the purified S. dysenteriae 1 LPS demonstrating the typical multiple banding pattern of smooth LPS. The final LPS product has residual amounts of protein (<5%, determined by Bradford assay) and DNA (<5%, determined by Hoechst stain) and is reactive with LPS serotype specific antibodies (anti-S. dysenteriae 1 LPS mAb MAB753 (Chemicon International) for S. dysenteriae 1 LPS; mAb 2E8 for S. flexneri 2a LPS; MAB755 (Chemicon) for S. sonnei LPS) by western blot or ELISA.

Quantitation of IpaB and IpaC Content in Invaplex$_{AR}$ by Immunoassay

The amount of IpaB and IpaC in Invaplex (artificial or native) was determined using a modified ELISA procedure. The ELISA used purified recombinant IpaB or IpaC proteins to generate standard curves for determination of the quantity of the antigens in the Invaplex preparations. Immulon 1B ELISA plates (ThermoLab Systems) were coated overnight at 4° C. with either 50 µl of recombinant IpaB, recombinant IpaC, or Invaplex$_{AR}$. Antigen was titrated (in triplicate) using 2-fold serial dilutions in carbonate coating buffer (0.2 M carbonate, pH 9.8) with starting concentrations of 125 ng/ml (IpaB), 200 ng/ml (IpaC), and 10 ug/ml (Invaplex). After washing and blocking with casein, affinity-purified monoclonal antibodies specific for IpaB (2F1) or IpaC (2G2) [32] were incubated with the antigen-coated plates for 2 hours. After washing, antigen-specific antibody was detected using anti-mouse immunoglobulin G (IgG) conjugated with alkaline phosphatase (Kirkegaard & Perry). Using the substrate para-nitrophenyl phosphate the optical density at 405 nm ($OD_{405}$) was measured using an ELISA plate reader (Molecular Devices, Menlo Park, Calif.) after a 60 minute incubation with substrate. Using the Softmax Pro 4.5 (Molecular Devices) program, a standard curve plotting $OD_{405}$ versus concentration (ng/ml) was determined. The concentration of the unknown samples were then interpolated from the standard curve.

Invaplex$_{AR}$ is designed to have IpaB and IpaC concentrations and an IpaC/IpaB ratio that is similar to HP Invaplex 24. The ratio of the quantity of IpaC to IpaB was determined for the Invaplex$_{AR}$ and compared to HP-Invaplex 24, the most pure form of Invaplex. The IpaC/IpaB molar ratio in HP Invaplex is approximately 8. This was determined by densitometry analysis of SDS-PAGE gels and quantitative antibody based assays for IpaB and IpaC. In addition the LPS content is expected to be at the same relative mass ratio (approximately 0.5 to 0.6 mg of LPS for every 1 mg of protein) that is found in HP-Invaplex.

Measurement of LPS in Invaplex

LPS content in Invaplex preparations was measured by determining the amount of 2-keto-3-deoxyoctonate (KDO) in each preparation [43] or by using the limulus amoebocyte lysate assay (Cambrex Inc.).

Method for Formation of Artificial Invaplex. Preparation of Invaplex$_{AR}$ for S. flexneri 2a, S. sonnei and S. dysenteriae 1

The purified components were mixed at ratios similar to that found in highly purified native Invaplex to form the artificial Invaplex. Analysis of the S. flexneri 2a HP Invaplex indicated that the IpaC/IpaB molar ratio was approximately 8.0 and the LPS to total protein ratio was approximately 0.56 mg LPS/mg total protein. Using these parameters as a guide for reconstituting Invaplex from purified IpaB, IpaC and LPS a series of experiments were conducted to create an Invaplex$_{AR}$. Once formed, the artificial Invaplex was purified by ion-exchange FPLC.

Purified, soluble IpaB and IpaC, each in their respective final buffers were mixed together at an IpaC/IpaB molar ratio of 8. After the IpaB and IpaC were mixed, the solution was slowly added to dry LPS powder (ratio of LPS to total protein is 0.56). LPS from any Shigella species can be used; for the described experiments S. flexneri 2a, S. sonnei or S. dysenteriae 1 LPS was used. The mixture was incubated at 37° C. for approximately 2 hours with shaking. Afterwards the protein/LPS mixture was diluted to 20 mM Tris-HCl, 0.10 M NaCl and 1.2 M urea to reduce the NaCl concentration prior to ion-exchange chromatography. The diluted mixture was then purified on a HiTrap™ Q HP anion exchange column.

Assembly Experiments: Formation of a S. flexneri Invaplex$_{AR}$

Preliminary assembly experiments accommodated the insolubility of IpaC by maintaining both IpaC and IpaB proteins in a buffer containing ≧4M urea. Once the IpaC/IpaB mixture was added to LPS, solubility was no longer an issue which permitted the eventual removal of the urea. Typically purified IpaC by itself will precipitate upon dilution. In preliminary mixing experiments the 8 IpaC/IpaB molar ratio was maintained by adding 8 µM HisTagIpaC to 1 µM IpaB in a final volume of 1 ml. Both proteins were initially prepared in 20 mM Tris-HCl, 0.5 M NaCl, 6 M urea, pH 7.9. The proteins were mixed in a glass test tube and incubated at 37° C. without shaking for 15 mins. Dry LPS (230 µg) in a separate glass tube was also incubated at 37° C. without shaking for 15 mins. After the 15 min incubation, the IpaB+IpaC mixture was used to solubilize the pre-warmed LPS by slowly adding the protein mixture down the side of the tube, followed by vortexing. No appreciable flocculation or precipitation was observed. The IpaB/IpaC/LPS mixture was then incubated at 37° C. with shaking (200 rpm) for 2 hrs. In preparation for ion exchange chromatography (IEC), the mixture was diluted five-fold with pre-warmed 20 mM Tris buffer, pH 9.0 to lower the salt concentration. No precipitation was observed as the mixture cooled to room temperature. For final purification, the diluted IpaB/IpaC/LPS mixture was applied to an anion exchange column (HiTrap™ Q HP) with Buffer A consisting of 20 mM Tris-HCl, pH 9.0 and Buffer B consisting of 1 M NaCl, 20 mM Tris-HCl, pH 9.0, and a step gradient of 0% (5 column volumes) to 24% (10 column volumes) to 50% (6 column volumes) to 100% Buffer B (5 column volumes). One ml fractions were collected from a 1 ml HiTrap™ Q HP column at an elution flow rate of 1 ml/min. Fractions from each step were analyzed for the presence of IpaB, IpaC and LPS by spotblot. The S. flexneri Invaplex$_{AR}$ eluted in the 50% B step (FIG. 2) which contained the greatest quantities of all three components (IpaB, IpaC and LPS) as determined by western blots and silver stained gels (FIG. 2A). When applied to a size exclusion column the IpaB/IpaC/LPS complex eluted at between the 1 MDa and 669 kKa standards which is the same size range as HP Invaplex.

Formation of S. dysenteriae 1 Artificial Invaplex and Larger Scale Production

The above experiment was repeated but with a ten-fold increase in reactants to increase the Invaplex$_{AR}$ yield. In addition S. dysenteriae 1 LPS was used instead of S. flexneri LPS. As such, 3.28 mg of IpaC in 20 mM Tris-HCl, 0.5 M NaCl, 6 M Urea, pH 7.9, was mixed with 0.62 mg IpaB in 20 mM Tris-HCl, 0.5 M NaCl, pH 7.9, in a total volume of 5 mls. The protein mixture and a separate tube of LPS (2.1 mg) was pre-warmed to 37° C. The IpaB+IpaC mixture was added to the LPS tube and vortexed to solubilize the LPS. No precipitation was observed. The reaction mixture was incubated at 37° C. with shaking (200 rpm) for 2 hours. Next pre-warmed IEC Buffer A (20 mM Tris-HCl, pH 9.0) was added to dilute the salt concentration 1:5 yielding a final volume of 25 mls. After cooling to room temperature, the diluted reaction mixture was applied to a 1 ml HiTrap™ Q HP IEC column and subjected to an Invaplex purification step gradient (see above). The *S. dysenteriae* 1 Invaplex$_{AR}$ eluted in the 50% Buffer B step. It contained IpaB, IpaC and *S. dysenteriae* 1 LPS. (FIG. 2C). Analysis of the 0.24 M and 1.0M NaCl peaks did not detect significant quantities of IpaB, IpaC or LPS. The yield of Invaplex$_{AR}$ production was approximately 10 to 20% of the amount of total protein used to initiate the assembly process.

Similar assembly experiments have been conducted for *S. sonnei* resulting in an InvaplexAR for *S. sonnei* (see FIG. 2B).

Large Scale Production of Invaplex$_{AR}$ of *Shigella flexneri* 2a

A fifty-fold increase in reactants was used to produce more Invaplex$_{AR}$ for advanced studies. Using an 8 IpaC/1 IpaB molar ratio, 16.4 mg of IpaC (in 20 mM Tris-HCl, 0.5 M NaCl, 6 M Urea, pH 7.9) was mixed with 3.1 mg IpaB (in 20 mM Tris-HCl, 0.5 M NaCl, pH 7.9) in a total volume of 20 mls. The protein mixture and a separate tube of *Shigella flexneri* 2a LPS (11.4 mg) were pre-warmed to 37° C. The IpaB+IpaC mixture was added to the LPS tube and vortexed to solubilize the LPS. The reaction mixture was incubated at 37° C. with shaking (200 rpm) for 2 hours. Next pre-warmed IEC Buffer A (20 mM Tris-HCl, pH 9.0) was added to dilute the salt concentration 1:5 yielding a final volume of 100 mls. After cooling to room temperature, the diluted reaction mixture was applied to a 5 ml HiTrap™ Q HP IEC column and subjected to an Invaplex purification step gradient (see above). The *S. flexneri* 2a Invaplex$_{AR}$ eluted in the 50% Buffer B step. It contained IpaB, IpaC and *S. flexneri* 2a LPS. Analysis of the 0.24 M and 1.0M NaCl peaks did not detect significant quantities of IpaB, IpaC or LPS. The yield of Invaplex$_{AR}$ production was approximately 9% of the amount of total protein used to initiate the assembly process.

Analysis of Invaplex$_{AR}$ Preparations by Electrophoresis and Western Blots for IpaB and IpaC The total protein composition of the Invaplex$_{AR}$ preparations was determined by stained SDS-PAGE gels. Western blots were used to determine the presence, size and relative concentrations of IpaB and IpaC. Silver stained gels were used to assess the LPS profile [18]. Monoclonal antibodies specific for either the IpaB or IpaC proteins were used to probe the nitrocellulose blots [32]. After probing with alkaline phosphatase-conjugated protein A, blots are developed with ASMX phosphate (Sigma) and Fast Red TR salt (Sigma). Video images of the blots are displayed on a Macintosh computer using a CCD video camera (Cohu) and captured with NIH Image software (version 1.62). Densitometry analysis of the digital images were performed with GelPro Image analysis software (version 2.0.10, Media Cybernetics, Inc.). The total protein gel profile and the IpaB and IpaC content should resemble that found in HP-Invaplex 24 or HP-Invaplex 50.

Size Exclusion Chromatography

Size-exclusion chromatography was used to determine if the components of Invaplex$_{AR}$ found in the ion-exchange peak are truly complexed. This is the same method used to produce HP-Invaplex. A Superose 6 HR 10/30 column (Amersham Pharmacia), calibrated with Blue Dextran 200 (2 MDa), thyroglobulin (669 kKa),and ovalbumin (43 kKa), was loaded with Invaplex$_{AR}$ (approximately 3 mg). Fractions (0.5 ml, flow rate 0.25 ml/min) were collected and analyzed by immuno-spot blot for the presence of IpaB, IpaC and LPS. All three Invaplex$_{AR}$ components (IpaB, IpaC and LPS) eluted in fractions between 2 MDa and 669 kKa indicating they are associated in a complex as they eluted at a size much greater than the individual components (43 kKa for IpaC; 62 kKa for IpaB). The SEC size of Invaplex$_{AR}$ is similar to the size where HP-Invaplex elutes.

Evaluation of S. dysenteriae 1 Invaplex$_{AR}$ in Tissue Culture model of Internalization Invaplex binds to and stimulates endocytosis in cultured mammalian cells. This property is dependent on the presence of the invasins IpaB and IpaC and utilizes host-cell acting during the endocytic process [38]. The Invaplex internalization assay is an in vitro model used to measure the functional activity of Invaplex preparations. The assay is modeled after the *Shigella* plaque assay [39]and *Shigella* uptake assays [40, 41]. The assay involves incubating $Invaplex_{AR}$ with BHK-21 fibroblast cells (60-70% confluent) in chamber slides. After incubation for 5, 15, 30, or 60 minutes the cells were washed 3× with PBS and formalin-fixed. Fixed cells were permeabilized with PBS supplemented with 0.1% Triton X-100 and 0.1% BSA (wash buffer) and probed with polyclonal mouse serum with specificity for LPS, IpaB, and IpaC. Bound polyclonal mouse antibodies were detected with GAM-IgG-Oregon Green 488 (Molecular Probes) followed by counterstaining with DAPI to identify the nuclei. The Invaplex treated cells were examined by fluorescent microscopy with digital image capturing. Both native and artificial *S. dysenteriae* 1 Invaplex were internalized by BHK cells with similar cytoplasmic staining pattern for both preparations indicating that the $Invaplex_{AR}$ maintains the capacity to stimulate internalization by mammalian cells (FIG. 4). This indicates that the assembly of recombinant IpaB and IpaC with *S. dysenteriae* 1 LPS into a complex isolated by ion-exchange FPLC has resulted in a synthetic product which maintains the same biological activity as the native complex.

Immunogenicity, Adjuvanticity and Protective Efficacy of Native and Artificial Invaplex Vaccines The mouse lung-infection [31] and the guinea pig keratoconjunctivits models [44] were used to determine whether intranasal immunization with *S. flexneri* 2a $Invaplex_{AR}$ stimulates a protective immune response that is effective against a homologous *S. flexneri* 2a challenge. Separate mouse studies were used to determine whether immunization with *S. sonnei* $Invaplex_{AR}$ could protect against a homologous *S. sonnei* challenge and against a heterologous challenge with *S. flexneri* 2a. Additional studies were conducted to assess the adjuvant activity of $Invaplex_{AR}$ using ovalbumin (OVA) as an immunogen. In the adjuvanticity experiments, immune responses induced after immunization with OVA alone were compared to immune responses induced with OVA combined with either native Invaplex, $Invaplex_{AR}$, or cholera toxin, an established, potent mucosal adjuvant. The guinea pig and mouse experiments were conducted at WRAIR under IACUC approved protocols.

Mouse Experiments

Four separate animal experiments have been completed to evaluate the immunogenicity, adjuvanticity, and protective efficacy of artificial Invaplex. Common methods were used in each experiment and are outlined in the following paragraph. Methods and materials specific to each study are indicated in separate sections.

Immunizations and Challenge

Mice were immunized on days 0, 14 and 28. A total antigen volume of 25 ul was delivered in 5 to 6 small drops applied to the external nares with a micropipette. Blood taken by tail bleed from all mice at days 0, 28 and 42 and 2 weeks post-challenge (day 63). On day 35 or 42 mice were euthanized followed by immediate collection of mucosal washes and removal spleen for in vitro proliferation and cytokine analysis *S. flexneri* 2a $Invaplex_{AR}$. Three weeks after the final immunization mice (15 per group) were challenged intranasally with a lethal dose ($1.6\times10^7$ cfu) of *S. flexneri* 2a (2457T) or with *S. sonnei* (Mosely, $8\times10^6$ cfu) as described for the mouse lung model [34]. Prior to intranasal immunization or challenge, mice are anesthetized with a mixture of ketamine hydrochloride (40 mg/kg) and xylazine (12 mg/kg). Challenged mice were monitored daily for two weeks for weight loss, fur ruffling and lethargy, with death used as an endpoint. Surviving mice were bled 14 days post-challenge (day 63).

*S. flexneri* 2a $Invaplex_{AR}$ Immunogenicity and Protection Study I

Separate groups of female Balb/c mice (10-15 mice/group) were immunized intranasally on day 0, 14, and 28 with 5 ug of either the native *S. flexneri* 2a Invaplex (lot JWJX) or 2.5 μg of artificial *S. flexneri* 2a $Invaplex_{AR}$ (Lot KF-D3D4) vaccines. Control animals were inoculated with saline. Blood was collected on day 0, 28, 42, and 63. Animals were challenged intranasally on day 49.

*S. flexneri* 2a $Invaplex_{AR}$ Immunogenicity and Protection Study II

Separate groups of female Balb/c mice (15-20 mice/group) were immunized intranasally on day 0, 14, and 28 with 5 ug of either the native *S. flexneri* 2a Invaplex (Lot JWJX) or 2.5 μg of artificial *S. flexneri* 2a $Invaplex_{AR}$ (lot KR-C5) vaccines. Control animals were inoculated with saline. Blood was collected on day 0, 28, 42, and 63. Lung and intestinal washes were collected on day 42 from 4 animals/group. Remaining animals were challenged intranasally on day 49.

*S. flexneri* 2a $Invaplex_{AR}$ Adjuvanticity Study

The ability of $Invaplex_{AR}$ to function as a mucosal adjuvant was determined in mice using ovalbumin (OVA) as a model protein antigen. Balb/cByJ mice (5 mice/group) were intranasally immunized on day 0, 14, and 28 with OVA (5 μg) alone, or OVA (5 μg) combined with either *S. flexneri* 2a $Invaplex_{AR}$ (lot KF-D3D4; 2.5 μg), native *S. flexneri* 2a Invaplex (Lot JWJX; 5 μg), or cholera toxin (CT; 5 μg). Blood was collected on day 0, 28, and 42. Control animals were inoculated with saline. Lung and intestinal washes were collected on day 42. Serum endpoint titers on day 0, 28 and 42 with specificity for Invaplex 24, Invaplex 50, LPS, OVA, IpaB and IpaC were determined by ELISA. Antigen-specific antibodies in mucosal washes were also assessed.

*S. sonnei* $Invaplex_{AR}$ Immunogenicity and Protection Study

The immunogencity and protective efficacy of *S. sonnei* $Invaplex_{AR}$ was determined in mice using a homologous (*S. sonnei* 53G) and heterologous (*S. flexneri* 2a 2457T) challenge. Balb/cByJ mice (10-15 mice/group) were intranasally immunized on day 0, 14, and 28 with *S. sonnei* $Invaplex_{AR}$ (lot KJ-D3D6; 2.5 μg), native *S. sonnei* Invaplex (Lot JOJP; 5 μg), or native *S. flexneri* 2a Invaplex (Lot JWJX; 5 μg). Control animals were inoculated with saline. Blood was collected on day 0, 28, and 42.

Guinea Pig Experiments

Guinea pigs (Hartley strain, 6 to 10 per group) were immunized intranasally with the artificial or native Invaplex vaccines (25 ug/dose). The dose volume (100 ul) was split equally between each nostril. Saline was used to immunize control animals. Guinea pigs were immunized on days 0, 14, and 28 and bled from the lateral ear vein on days 0, 28, 42, and 14 days after challenge. Prior to intranasal immunization, guinea pigs were anesthetized with a mixture of ketamine (40 mg/kg) and xylazine (4 mg/kg). Three weeks after the third immunization guinea pigs were challenged intraocularly with *S. flexneri* 2a (strain 2457T) and observed daily for 5 days to assess the degree of inflammation and keratoconjunctivitis as previously described [44].

ELISA

ELISA assays are used to measure antigen specific IgA and IgG antibodies in sera and mucosal secretions, including lung and intestinal lavages and stool extracts from immunized and/or challenged mice and guinea pigs [18, 29, 46]. Antigens used in ELISAs, including purified *S. flexneri* 2a LPS, *S. sonnei* LPS, water-extracted *Shigella* antigens, purified IpaB and IpaC proteins, and *S. flexneri* 2a native Invaplex and OVA were coated onto ImmunIon IB 96-well ELISA plates (ThermoLab Systems) overnight at 4° C. After blocking with 2% casein (in Tris-saline buffer, pH 7.5) sera and mucosal washes were serially diluted in duplicate and incubated with the antigen-coated plates for 4 hours at 25° C. After washing with PBS containing 0.05% Tween 20, antigen-specific antibody is probed with alkaline phosphatase conjugated anti-mouse IgG or anti-mouse IgA (Kirkegaard & Perry). Alkaline phosphatase activity was detected with p-nitrophenyl phosphate (1 mg/ml). After a 30-min incubation in substrate, the optical density ($OD_{405}$) was measured using an ELISA plate reader (Molecular Devices, Menlo Park, Calif.). Endpoint titers were determined for each animal and was used to calculate geometric mean titers for each group at each time point. Typically animals intranasally immunized with Invaplex respond with a 4 to 8-fold higher serum (IgG and IgA) and mucosal (lung and intestine) IgA titers to *Shigella* antigens as compared to preimmune samples or saline control animals.

Total IgA Assay

A capture enzyme immunoassay was used to determine total IgA concentrations in mucosal samples. Sample concentrations were determined from standard curves, using purified mouse IgA assayed in parallel. Specific mucosal IgA activities were calculated by dividing the endpoint titer for each individual mucosal sample by the concentration of total IgA within the same sample [47].

Antigen Stimulation of Cultured Lymphocytes from Mice Immunized with Invaplex$_{AR}$ Lymphocyte proliferation upon antigen stimulation was determined using splenocytes collected from Invaplex-immunized mice and naive mice. Mononuclear cells ($2 \times 10^5$ per well) were incubated with Invaplex, IpaB, or IpaC or *S. flexneri* 2a LPS preparations. Simultaneously in separate microtiter wells, splenocytes were stimulated with concanavalin A to provide positive controls. Negative controls included cells incubated with complete medium alone and cells from naive mice stimulated with antigen. After incubation with antigen for 4 to 7 days, cell proliferation was measured by a non-radioactive assessment of dehydrogenase activity using MTS (Promega) [48]. There is a strong correlation with increasing optical density readouts in this assay and the number of viable cells in a well. Prior to measuring proliferation, cell culture supernatants were collected on days 3 and 5 for cytokine measurements (see below). Stimulation indices (SI) were calculated by dividing the mean optical density of antigen-stimulated cells by the mean optical density of medium-only stimulated cells. The SI of cells from mice immunized with Invaplex was compared to the SI of cells from non-immunized mice.

Antigen-Specific Systemic Antibody Response after Intranasal Immunization with Invaplex$_{AR}$ The immunogenicity of artificial *S. flexneri* 2a Invaplex (Invaplex$_{AR}$), manufactured from individual purified components rather than the virulent organism (native Invaplex) was evaluated in mice. Groups of mice (n=6-10) were intranasally immunized on day 0, 14, and 28 with native *S. flexneri* 2a Invaplex 24 (5 or 10 µg), Invaplex$_{AR}$ (2.5 µg), purified IpaB (2.5 µg), purified IpaC (2.5 µg), LPS (2.5 µg), or saline. Three weeks after the third immunization (day 49), the mice were challenged with *Shigella flexneri* 2a (2457T). Blood collected on day 0, 28, 42, and 63 was analyzed by ELISA for serum IgG and IgA responses to Invaplex 50, Invaplex 24, purified LPS, IpaB and IpaC. FIGS. 5 and 6 outline the serum IgG and IgA endpoint titers determined in blood collected on day 42 (two weeks after the third immunization).

Saline-inoculated mice and preimmune sera from immunized mice did not have detectable levels of antigen-specific antibodies (data not shown). Immunization with *S. flexneri* 2a Invaplex$_{AR}$ induced serum IgG and IgA responses to Invaplex 50 and Invaplex 24 of comparable magnitude to those induced with native Invaplex 24 (FIG. 5), and significantly higher (p<0.001) than those induced after inoculation with saline. A two-fold increase in the amount of native Invaplex (lot JWJX) used for immunization did not result in an increase in the magnitude of the Invaplex 50, LPS, or Invaplex 24-specific serum IgG or IgA responses measured on day 42 (FIG. 5). Immunization with purified IpaB resulted in a strong IpaB-specific (FIG. 6) and Invaplex 24-specific response (GMT>5760 and 3800, respectively) and a moderate response to Invaplex 50 (GMT 950). Immunization with purified LPS did not induce a detectable serum IgG or IgA response to any of the antigens used in ELISA in the majority (5/6) of mice in the vaccine group. Similarly, immunization with purified IpaC also did not induce a detectable immune response to any of the antigens assayed, including a IpaC-specific ELISA. Interestingly, the mice immunized with Invaplex$_{AR}$ had among the highest IpaC-specific endpoint titers (FIGS. 6 and 8, significantly higher (p<0.001) than those induced after immunization with native Invaplex.

Protection of Mice from a Lethal Challenge of *S. flexneri* after Intranasal Immunization with Invaplex$_{AR}$ The lethal lung model entails intranasal inoculation of mice with a lethal dose of shigellae which establish an infection of the lungs leading to severe weight loss, pneumonia and ultimately death over the observation period of two weeks. Three weeks after intranasal immunization with *S. flexneri* 2a Invaplex$_{AR}$ or native Invaplex mice were challenged with a lethal dose of *S. flexneri* 2a (strain 2457T). In naive mice (treated with saline) 11 of 13 mice died with a mean maximum weight loss of 31.4% of the pre-challenge weight (see Table 1). All mice immunized with *S. flexneri* 2a Invaplex$_{AR}$ (p<0.001) or native Invaplex (p<0.001) survived the lethal challenge with *S. flexneri* 2a. With respect to weight loss (which is likely a more sensitive indicator of protective immunity) mice immunized with Invaplex$_{AR}$ lost less of their pre-challenge weight (21.3%) as compared to 23.8% to 26.0% weight loss in the native Invaplex-immunized mice. Furthermore the day of weight rebound (an indication of recovery from the challenge) was day 7 for Invaplex$_{AR}$ and day 13 (native Invaplex, 5 µg) or day 7 (native Invaplex, 10 µg).

In addition the protective capacity of the individual components (IpaB, IpaC and LPS) used to construct Invaplex$_{AR}$ were also evaluated in the mouse lethal lung model (see Table 1). Immunization with purified LPS and purified IpaC did not protect mice from death (both P>0.05) and although immunization with IpaB protected 5 of 6 mice from a lethal challenge the mice never regained weight and remained symptomatic (low weight, ruffled fur) through the end of the observation period. The mean maximum weight loss after challenge was 29.9% for LPS, 31.0% for IpaB and 33.9% for IpaC all of which are very close to the naïve mice weight loss value of 31.4%.

The results of the challenge of Invaplex$_{AR}$ mice with a lethal dose of *S. flexneri* 2a indicate that Invaplex$_{AR}$ stimulates a level of protection that is comparable to or exceeds that of native Invaplex. Furthermore, it appears that the complex of IpaB, IpaC and LPS is required in that individual components are incapable of stimulating a fully effective protective immune response.

and significantly higher levels (p<0.001) of IpaB-specific IgA. Minimal IpaC-specific intestinal IgA was elicited after immunization with any of the Invaplex vaccine preparations (Tables 7 and 8).

Intranasal immunization with Invaplex$_{AR}$ elicited strong antibody responses in the lung, directed to LPS, Invaplex 50, IpaB and IpaC (FIG. 8 and Tables 7 and 8). Minimal levels of LPS-specific IgA were induced in the lung after immunization with native Invaplex with undetectable levels of antibodies specific for Invaplex 50, IpaB and IpaC.

Antigen-Specific Cellular Proliferative Response and Secreted Cytokine Profiles after Intranasal Immunization with Invaplex$_{AR}$ Splenocytes collected from immunized mice on day 35 were stimulated in vitro with Invaplex 24, IpaB, or IpaC to assess induction of antigen-specific cell-mediated responses. Proliferation of cells after incubation with antigen indicates prior exposure and immunological memory. Concavalin A (ConA), which non-specifically activates T cell proliferation, was used as a positive control to demonstrate viable cell levels. Stimulation indices (Sis) after stimulation with ConA ranged from 13.8 to 15.9 (Table 2). Cells from saline inoculated animals did not proliferate after incubation with Invaplex, IpaB, or IpaC. Splenocytes from animals (4/4) immunized with Invaplex$_{AR}$ proliferated after incubation with Invaplex (SI=10.2), IpaB (SI=8.7), and IpaC (SI=6.9) indicating immunological memory to these antigens was present.

TABLE 1

Lethal Challenge of mice immunized with *S. flexneri* 2a InvaplexAR or native Invaplex[1].

| Immunizing Antigen | Maximum Wgt Loss (%) | Day of 50% Wgt recovery | No. Survivors | No. Dead | Total No. of Animals | % Protection† | P Value* |
|---|---|---|---|---|---|---|---|
| *S. flexneri* 2a Invaplex$_{AR}$, 2.5 µg | 21.32 | 7 | 15 | 0 | 15 | 100% | <0.001 |
| Invaplex 24 JWJX, 5 µg | 26.02 | 13 | 15 | 0 | 15 | 100% | <0.001 |
| Invaplex 24 JWJX, 10 µg | 23.81 | 7 | 12 | 0 | 12 | 100% | <0.001 |
| *S. flexneri* 2a LPS, 2.5 µg | 29.95 | 8 | 3 | 3 | 6 | 40.9% | 0.262 |
| Purified 1paB, 2.5 µg | 30.97 | >14 | 5 | 1 | 6 | 80.3% | 0.010 |
| Purified HisTagIpaC, 2.5 µg | 33.91 | >14 | 1 | 5 | 6 | 1.5% | 1.000 |
| 0.9% Saline | 31.35 | 10 | 2 | 11 | 13 | 0% | — |

[1]Three weeks after the final immunization, mice were intranasally challenged with 1.5 × 10^7 cfu of *S. flexneri* 2a,. Weight loss and symptoms were monitored daily for 14 days.
†% Protection = [(%Death$_{Control}$ - % Death$_{Vaccinees}$)/% Death$_{Control}$] × 100
*Fisher Exact Test Antigen-Specific Mucosal Antibody Response After Intranasal Immunization with Invaplex$_{AR}$ Intestinal and lung washes collected on day 35 from mice immunized with *S. flexneri* 2a Invaplex$_{AR}$ or native Invaplex were assessed by ELISA for antigen-specific IgA levels. Immunization with Invaplex$_{AR}$ induced levels of LPS and Invaplex-specific intestinal IgA that were comparable to levels induced by immunization with native Invaplex (FIG. 7)

The IpaB and IpaC-specific proliferative responses in groups immunized with Invaplex$_{AR}$ were significantly higher (P<0.01) than the proliferative responses in groups immunized with native Invaplex. Splenocytes from 4/4 animals immunized with native Invaplex proliferated after incubation with Invaplex (SI=6.8). Low to undetectable levels of proliferation occurred in splenocytes from mice immunized with native Invaplex after ex vivo incubation with IpaB (1/4 mice) or IpaC (0/4 mice).

TABLE 2

Antigen-specific cellular proliferation of splenocytes from mice intranasally immunized with S. flexneri 2a Invaplex$_{AR}$ or native Invaplex after in vitro stimulation.

<table>
<tr><th colspan="2"></th><th colspan="4">Cellular proliferative responses after in vitro stimulation[a] with:</th></tr>
<tr><th>Grp.</th><th>Treatment</th><th>S. flexneri 2a Invaplex 24 (1 µg/ml)</th><th>IpaB (5 µg/ml)</th><th>IpaC (5 µg/ml)</th><th>ConA (5 µg/ml)</th></tr>
<tr><td>31</td><td>S. flexneri 2a Invaplex$_{AR}$ (KR-C5; 2.5 µg)[b]</td><td>10.2 ± 3.4[c]*, ** (4/4)</td><td>8.7 ± 2.2*, ** (4/4)</td><td>6.9 ± 3.9*, ** (4/4)</td><td>14.2 ± 4.5*, ** (4/4)</td></tr>
<tr><td>32</td><td>S. flexneri 2a native Invaplex 24 (JWJX; 2.5 µg)</td><td>6.8 ± 1.5* (4/4)</td><td>2.2 ± 1.4 (1/4)</td><td>1.6 ± 0.9 (0/4)</td><td>15.9 ± 2.3 (4/4)</td></tr>
<tr><td>33</td><td>0.9% saline</td><td>1.1 ± 0.4 (0/4)</td><td>1.2 ± 0.8 (0/4)</td><td>1.8 ± 1.1 (0/4)</td><td>13.8 ± 3.3 (4/4)</td></tr>
</table>

[a] proliferative responses in splenocytes were determined after stimulation in vitro for 3 days with ConA and 5 days with S. flexneri 2a Invaplex 24 (lot JWJX), IpaB or IpaC.
[b] (lot number; immunization dose)
[c] Mean stimulation index ± ISD (number of responders/total number in group)
*P < 0.05 as compared to saline-inoculated group (unpaired t test).
**P < 0.01 as compared to native Invaplex-immunized group (unpaired t test).

Confirmation of Protection of Mice from a Lethal Challenge of S. flexneri after Intranasal Immunization with Invaplex$_{AR}$ using a Different Lot of Invaplex$_{AR}$ The experiment describing protection with Invaplex$_{AR}$ in the mouse lethal lung model was repeated with a different lot of S. flexneri 2a Invaplex$_{AR}$. In addition the evaluation of the purified components was repeated along with mice immunized with mixtures of two purified components (IpaB+IpaC; IpaB+LPS; IpaC+LPS). For this challenge, mice were inoculated intranasally with a slightly higher challenge dose (1.6× 10$^6$ cfu) of S. flexneri 2a (strain 23457T). In naive mice (treated with saline) 14 of 14 mice died with a mean maximum weight loss of 34.5% of the pre-challenge weight (see Table 3). Mice immunized with S. flexneri 2a Invaplex$_{AR}$ (13 of 14 survived; p<0.001) survived the lethal challenge with S. flexneri whereas mice immunized with native Invaplex had a much lower survival rate for the challenge dose used in this experiment (See Table 3). With respect to weight loss mice immunized with Invaplex$_{AR}$ lost less of their pre-challenge weight (26.6%) as compared to 31.6% weight loss in the native Invaplex-immunized mice and 34.5% in the mice inoculated with saline.

The protective capacity of the individual components (IpaB, IpaC and LPS) or pairs of purified components used to construct Invaplex$_{AR}$ confirmed previous results in that IpaC and LPS are not protective. Purified IpaB was not protective either. (see Table 3). Mixtures of two of the purified components resulted in protection in the IpaB+LPS combination and the IpaC+LPS combination whereas the IpaB+IpaC combination was not fully protective.

The results of the second experiment evaluating the protective capacity of Invaplex$_{AR}$ clearly shows that Invaplex$_{AR}$ stimulates a level of protection that exceeds that of native Invaplex. Furthermore, it appears that the individual components (IpaB, IpaC or LPS) are incapable of stimulating a fully effective protective immune response.

TABLE 3

Lethal Challenge of mica immunized with S. flexneri 2a InvaplexAR or native Invaplex[1]

| Antigen | Maximum Wgt Loss (%) | Day of 50% Wgt Recovery | No. Survivors | No. Dead[1] | Total No. of Animals | % Protection[2] | P Value[3] |
|---|---|---|---|---|---|---|---|
| IVP$_{AR}$ S.flex 2a KR-C5, 2.5 µg | 26.6 | 10 | 13 | 1 | 14 | 92.9 | <0.001 |
| IVP$_{24}$ S.flex2a JWJX,5 µg | 31.6 | — | 4 | 10 | 14 | 28.6 | 0.098 |
| 0.9% Saline | 34.5 | — | 0 | 14 | 14 | 0 | |
| S.flex2a LPS, 2.5 µg | 32.7 | — | 0 | 14 | 14 | 0 | NS |
| IpaB, 2.5 µg | 29.8 | 13 | 1 | 13 | 14 | 7.1 | NS |
| HisTag IpaC, 2.5 µg | 38 | — | 0 | 14 | 14 | 0 | NS |
| S.flex2a LPS/ IpaB, 2.5 µg each | 24 | 8 | 14 | 0 | 14 | 100 | <0.001 |

TABLE 3-continued

Lethal Challenge of mice immunized with S. flexneri 2a InvaplexAR or native Invaplex[1]

| Antigen | Maximum Wgt Loss (%) | Day of 50% Wgt Recovery | No. Survivors | No. Dead[1] | Total No. of Animals | % Protection[2] | P Value[3] |
|---|---|---|---|---|---|---|---|
| S.flex2a LPS/ HisTag IpaC, 2.5 µg each | 25 | 8 | 13 | 1 | 14 | 92.9 | <0.001 |
| IpaB/HisTag IpaC, 2.5 µg each | 26.7 | 8 | 5 | 9 | 14 | 37.7 | 0.041 |

[1]Three weeks after the final immunization, mice were intranasally challenged with $1.6 \times 10^7$ cfu of S. flexneri 2a,. Weight loss and symptoms were monitored daily for 14 days.
[2]% Protection = [(% Death$_{Control}$ - % Death$_{Vaccinees}$)/% Death$_{Control}$] × 100
[3]Fisher Exact Test

S. sonnei Invaplex$_{AR}$ Murine Immunogenicity and Protection Study

Serum antibody responses directed to S. sonnei Invaplex 50, S. sonnei LPS, IpaB and IpaC were determined by ELISA. Mice inoculated with saline (negative control) did not have detectable levels of antigen-specific serum IgG or IgA on day 42 (Table 4). Similar S. sonnei Invaplex 50 and LPS-specific serum IgG and IgA endpoint titers were achieved after immunization with S. sonnei Invaplex$_{AR}$ and native Invaplex (Table 4). Groups of mice immunized with S. sonnei Invaplex$_{AR}$ had higher levels of IpaB-specific serum IgG (GMT>5760, P<0.001) as compared to groups of mice immunized with native S. sonnei Invaplex (GMT 546). Animals immunized with Invaplex$_{AR}$ had an anti-IpaC serum IgG mean titer of 1091 (P<0.001) whereas animals immunized with native Invaplex or saline had undetectable levels of IpaC-specific IgG.

Protection of Mice from a Lethal Challenge of S. sonnei or Heterologous S. flexneri after Intranasal Immunization with S. sonnei Invaplex$_{AR}$ The protective capacity of InvaplexAR was also evaluated for an InvaplexAR manufactured from purified S. sonnei LPS and recombinant IpaB and IpaC using the mouse lethal lung model. It was compared to native S. sonnei Invaplex. In addition the capacity of S. sonnei Invaplex$_{AR}$ to protect against a heterologous S. flexneri challenge was also evaluated. In nave mice (treated with saline) 15 of 15 mice died with a mean maximum weight loss of 23.4% of the pre-challenge weight (see Table 5). Mice immunized with S. sonnei Invaplex$_{AR}$ survived (15 of 15 survived; p<0.001) the lethal challenge with S. sonnei whereas mice immunized with native Invaplex also exhibited solid protection (14 of 14 survived, P<0.001) (See Table 5). With respect to weight loss, mice immunized with S. sonnei Invaplex$_{AR}$ lost 7.7% of their pre-challenge weight as compared to 9.2% weight loss in the native S. sonnei Invaplex-immunized mice and 23.4% in the mice inoculated with saline.

Interestingly, the S. sonnei Invaplex$_{AR}$ also provided significant protection (15 or 15 challenged mice survived, P<0.001)) against a heterologous S. flexneri 2a challenge

TABLE 4

Antigen-specific serum IgG and IgA endpoint titers on day 42 in mice after intranasal immunization with S. sonnei Invaplex$_{AR}$ or native S. sonnei Invaplex 50

| | S.sonnei Invaplex 50 | | S. sonnei LPS | | IpaB | IpaC |
|---|---|---|---|---|---|---|
| | IgG | IgA | IgG | IgA | IgG | IgG |
| Saline | 90 ± 0[c,d] | 45 ± 0 | 90 ± 0 | 45 ± 0 | 90 ± 0 | 90 ± 0 |
| Native S. sonnei Invaplex 50 (5 µg)[a] | 2183 ± 789 | 1254 ± 322 | 103 ± 40 | 157 ± 40 | 546 ± 483 | 90 ± 0 |
| Artificial S. sonnei Invaplex$_{AR}$ (2.5 µg)[b] | 5014 ± 1288** | 2864 ± 36** | 136 ± 117 | 313 ± 224* | >5760** | 1091 ± 1172** |

[a]Group 6
[b]Group 3
[c]Geometric mean endpoint titer ± 1 standard deviation
[d]Comparisons between groups were accomplished using two-way ANOVA analysis of natural log-transformed endpoint titers.
*p < 0.05 as compared with native S. sonnei Invaplex 50
**p < 0.001 as compared with native S. sonnei Invaplex 50 suggesting that the immune response to either IpaB or IpaC may contribute significantly to the protective immune response.

The results of this experiment evaluating the protective capacity of S. sonnei Invaplex$_{AR}$ clearly shows that Invaplex$_{AR}$ from another Shigella species stimulates a level of protection that is comparable to that of native Invaplex.

TABLE 5

Lethal Challenge of mice immunized with S. sonnei Invaplex$_{AR}$ or native S. sonnei Invaplex[1].
Stimulation of homologous and heterologous immunity

| Antigen | Challenge Agent | Maximum Wgt Loss (%) | Day of 50% Wgt Recovery | No. Survivors | No. Dead[1] | Total No. of Animals | % Protection[2] | P Value[3] |
|---|---|---|---|---|---|---|---|---|
| Saline | S. sonnei | 23.4 | — | 0 | 15 | 15 | 0 | — |
| Sonnei IVP-AR-KJD3D6 2.5 ug | S. sonnei | 7.7 | 3 | 15 | 0 | 15 | 100 | <0.001 |
| IVP50 JOJP 5 ug 3x | S. sonnei | 9.2 | 7 | 14 | 0 | 14 | 100 | <0.001 |
| Saline | S. flexneri 2a | 35.1 | — | 0 | 15 | 15 | — | — |
| Sonnei IVP-AR 2.5 ug | S. flexneri 2a | 31.0 | 9 | 15 | 0 | 15 | 100 | <0.001 |
| S. flex 2a JWJX 5 ug 3x (Nasal) | S. flexneri 2a | 25.0 | — | 11 | 3 | 14 | 78.6 | <0.001 |

[1]Three weeks after the final immunization, mice were intranasally challenged with $1.6 \times 10^7$ cfu of S. flexneri 2a or $8 \times 10^6$ cfu S. sonnei, as indicated. Weight loss and symptoms were monitored daily for 14 days.
[2]% Protection = [(% Death$_{Control}$ - % Death$_{Vaccinees}$)/% Death$_{Control}$] × 100
[3]Fisher Exact Test Protection of Guinea Pigs with S. flexneri 2a Invaplex$_{AR}$ using the Guinea Pig Keratoconjunctivitis Model The guinea pig keratoconjunctivitis model is used to evaluate Shigella vaccines and is often used as the precursor to human trials. The model involves infection of the guinea pig eyes with Shigella which establish infection in the corneal epithelium. This outcome (severe keratoconjunctivitis) is a result of invasion of the corneal epitheilium by the shigellae and the subsequent inflammatory response by the host not unlike that observed in the human intestinal tract.

In this experiment guinea pigs were immunized three time intranasally with either S. flexneri 2a InvaplexAR or native Invaplex. A saline control group was also utilized. Three weeks after the final immunization animals were challenged ocularly with S. flexneri 2a. Both the InvaplexAR (90% protection, P<0.001) and native Invaplex (100% protection, P<0.001) provided solid protection (See Table 6) indicating that the Invaplex$_{AR}$ is comparable to the native Invaplex.

TABLE 6

Protection against Shigella infection in guinea pigs with S. flexneri 2a Invaplex$_{AR}$ using the keratoconjunctivitis model.

| Treatment | # positive[1] | # Negative | % protection[2] | P value[3] |
|---|---|---|---|---|
| S. flexneri 2a native Invaplex 50, 25 µg/dose | 0 | 10 | 100% | <0.001 |
| S. flexneri 2a Invaplex$_{AR}$, 25 µg/dose | 1 | 9 | 90% | <0.001 |
| IpaB (25 µg) + IpaC (25 µg) per dose | 4 | 6 | 40% | 0.01 |
| IpaB (25 µg) + IpaC (25 µg) + LPS (25 µg) per dose | 0 | 10 | 100% | <0.001 |
| (0.9% Saline) | 10 | 0 | 0% | — |

[1]Guinea pigs were challenged intraocularily with $1 \times 10^8$ cfu of S. flexneri 2a. Eyes were evaluated on day 5 post-infection for keratoconjunctivitis as described by Hartman et al. [44]
[2]% Protection = [(%Disease$_{Control}$ - % Disease$_{Vaccinees}$)/% Disease$_{Control}$] × 100
[3]Fisher Exact Test S. flexneri 2a Invaplex$_{AR}$ Murine Adjuvanticity Study Intranasal immunization with OVA alone or OVA combined with CT or pre-immune samples from immunized animals (day 0) did not induce detectable levels of serum IgG or IgA with specificity to S. flexneri 2a Invaplex 50, S. flexneri 2a Invaplex 24 (FIG. 9), S. flexneri 2a LPS (FIG. 10), IpaB or IpaC (FIG. 11). Immunization with OVA combined with either Invaplex$_{AR}$ or native Invaplex induced similar Invaplex 50, Invaplex 24 and LPS-specific serum IgG and IgA endpoint titers (FIGS. 9 and 10. Endpoint titers against purified IpaB (p<0.05) and IpaC (p≦0.001) were higher in mice immunized with OVA+Invaplex$_{AR}$ as compared to mice immunized with OVA+native Invaplex (FIG. 11). Comparable levels of OVA-specific serum IgG and IgA were induced in mice immunized with OVA combined with Invaplex$_{AR}$, native Invaplex, or CT on day 42 and were significantly higher (p≦0.001) than the responses induced in mice after immunization with OVA alone (FIG. 12).

Antigen-specific antibodies in lung washes were also assessed by ELISA to investigate the mucosal immune responses induced after immunization (FIG. 13). Immunization with OVA combined with Invaplex$_{AR}$ induced similar levels of LPS and Invaplex 24-specific IgG and IgA in lung washes as compared to responses after immunization with OVA combined with native Invaplex and higher than the levels induced after immunization with OVA alone, or OVA combined with CT. Similar levels of OVA-specific lung IgG and IgA were induced after immunization with OVA combined with Invaplex$_{AR}$, native Invaplex, or CT which were significantly (p<0.001) higher than those induced after immunization with OVA alone. Moderate levels of LPS and Invaplex-specific IgA in intestinal washes (data not shown) were detected in washes from mice immunized with OVA combined with Invaplex$_{AR}$ or native Invaplex and were undetectable in mice immunized with OVA alone or OVA combined with CT. OVA-specific intestinal IgA responses were below levels of detection in all samples assayed.

TABLE 7

Anti-IpaB and anti-IpaC serum (day 42) and mucosal (day 35) antibody levels after intranasal immunization of mice with S. flexneri 2a Invaplex or Invaplex$_{AR}$

| Study Name | Treatment | Anti-IpaB | | | Anti-IpaC | | |
|---|---|---|---|---|---|---|---|
| | | Serum IgG[a] | Lung IgA | Intestinal IgA | Serum IgG | Lung IgA | Intestinal IgA |
| S. flexneri 2a Invaplex$_{AR}$ Mouse Study I | Invaplex (5 μg) | >5760 (>5760) | ND | ND | 136 ± 117 (90–360) | ND | ND |
| | Invaplex$_{AR}$ (2.5 μg) | >5760 (>5760) | ND ND | ND ND | 1440 ± 4593* (90–11520) | ND ND | ND ND |
| | Saline | 90 ± 0 (90 – 90) | | | 90 ± 90) (90 – 90 | | |
| S. flexneri 2a Invaplex$_{AR}$ Mouse Study II | Invaplex (5 μg) | TBD | 2 ± 0 (2 – 2) | 3 ± 1 (2 – 4) | TBD | 2 ± 0 (2 – 2) | 2 ± 0 (2 – 2) |
| | Invaplex$_{AR}$ (2.5 μg) | TBD | 54 ± 58* (8 – 128) | 64 ± 54* (16 – 128) | TBD | 5 ± 15 (2 – 32) | 2 ± 0 (2 – 2) |
| | Saline | TBD | 2 ± 0 (2 – 2) | 2 ± 0 (2 – 2) | TBD | 2 ± 0 (2 – 2) | 2 ± 0 (2 – 2) |
| S. flexneri 2a Invaplex$_{AR}$ Adjuvanticity Study | Invaplex + OVA | 2507 ± 2366 (90 – 90) | ND | ND | 157 ± 148 (90 – 360) | ND | ND |
| | Invalpex$_{AR}$ + OVA | >5760* (>5760) | ND | ND | 950 ± 2318* (90 ± 5760) | ND | ND |
| | OVA | 90 ± 0 (90 – 90) | ND | ND | 90 ± 0 (90 – 90) | ND | ND |

[a]Serum responses in the S. flexneri 2a Invaplex$_{AR}$ Mouse Study I are bllod collected on day 42. Serum responses in the S. flexneri 2a Invaplex$_{AR}$ Adjuvanticity Study are from blood collected on day 35.
[b]Geomean ± 1 standard deviation from the mean (n = 5 mice/group) (range of endpoint titers)
*Significantly higher endpoint titers (one way ANOVA of log transformed endpoint titers; p ≦ 0.001) as compared to endpoint titers of animals immunized with native Invaplex.
ND; not determined,
TBD; to be determined

TABLE 8

Antigen-specific serum IgG and IgA endpoint titers on day 42 in guinea pigs intranasally immunized with native Invaplex, Invaplex$_{AR}$, or mixtures of IpaB and IpaC.

| | ELISA Antigen | | | | | |
|---|---|---|---|---|---|---|
| | S. flexneri 2a Invaplex 50 | | S. flexneri 2a LPS | | IpaB | IpaC |
| Treatment | IgG | IgA | IgG | IgA | IgG | IgG |
| S. flexneri 2a Invaplex (lot 1307; 25 μg) | 827 ± 1046[b] (180 – 2880) | 475 ± 1148 (180 – 2880) | 1091 ± 2873 (180 – 5760) | 827 ± 1018 (360 – 2880) | 1712 ± 2305 (720 –≧ 5760) | 90 ± 0 (90 – 90) |
| S. flexneri 2a Invaplex$_{AR}$ (lot KR-C5; 25 μg) | 4073 ± 2160* (1440 –≧ 5760) | 856 ± 360 (720 – 2880) | 2880 ± 2700 (360 –≧ 5760) | 827 ± 1046 (720 – 2880) | All > 5760* (>5760) | All > 5760* (>5760) |
| IpaB + IpaC (25 μg + 25 μg) | 1211 ± 1034 (360 – 2880) | 255 ± 104 (180 – 360) | 90 ± 0 (90 – 90) | 45 ± 0 (45 – 45) | All >5760* (>5760) | 3629 ± 2494* (1440 –≧ 5760) |
| Saline | 90 ± 0 (90 – 90) | 45 ± 0 (45 – 45) | 90 ± 0 (90 – 90) | 45 ± 0 (45 – 45) | 90 ± 0 (90 – 90) | 90 ± 0 (90 – 90) |

[a]Serum responses in the S. flexneri 2a GMP Stability and Invaplex$_{AR}$ guinea pig study are from blood collected on day 42.

Method for Formation and Evaluation of Artificial Invaplex Complexed with an Antibiotic or other Therapeutic Molecule for Intracellular Delivery Many therapeutic biochemicals, including antibiotics, are often ineffective against intracellular target because they are unable to cross mammalian cell membranes or because they require high extracellular concentrations to achieve therapeutic concentrations inside of mammalian cells. The artificial Invaplex provides a mechanism to create a complex of invasins, LPS and antibiotic by mixing the components during the assembly stage for creating artificial Invaplex. Once assembled, the native properties of Invaplex allow it to transport the complexed antibiotic or therapeutic molecule into mammalian cells.

Purified, soluble IpaB and IpaC, each in their respective final buffers are mixed together at an IpaC/IpaB molar ratio of 8. After the IpaB and IpaC are mixed, a solution of antibiotic, for example gentamicin at 5 to 100 μg/ml, is added to the mixture. Next the IpaB, IpaC and antibiotic solution is slowly added to dry LPS powder (ratio of LPS to total protein is 0.56). LPS from any Shigella species can be used; for the described experiments S. flexneri 2a, S. sonnei or S. dysenteriae 1 LPS was used. The mixture is incubated at 37° C. for approximately 2 hours with shaking. Afterwards the protein/LPS/antibiotic mixture is diluted to 20 mM Tris-HCl, 0.10 M NaCl and 1.2 M urea to reduce the NaCl concentration prior to ion-exchange chromatography. For final purification, the diluted IpaB/IpaC/LPS/antibiotic mixture is applied to an anion exchange column (HiTrap™ Q HP) with Buffer A consisting of 20 mM Tris-HCl, pH 9.0 and Buffer B consisting of 1 M NaCl, 20 mM Tris-HCl, pH 9.0, and a step gradient of 0% (5 column volumes) to 24% (10 column volumes) to 50% (6 column volumes) to 100% Buffer B (5 column volumes). One ml fractions were collected from a 1 ml HiTrap™ Q HP column at an elution flow rate of 1 ml/min. Fractions from each step were analyzed for the presence of IpaB, IpaC and LPS by spotblot. The fractions containing IpaB, IpaC and LPS are the artificial Invaplex fractions.

The effectiveness of the artificial Invaplex-antibiotic complex will be evaluated in its ability to kill intracellular microorganisms such as shigellae growing in tissue culture cells. The artificial Invaplex-antibiotic complex will be incubated with *Shigella*-infected tissue culture cells. After 2 to 24 hours the number of intracellular *Shigella* will be determined by plating lysates of the treated cells (and untreated control cells) on trypticase soy agar plates to determine the level intracellular killing in the cells treated with the artificial Invaplex-antibiotic complex.

Further variations and modification of the foregoing will be apparent to those skilled in the art and are intended to be encompassed by the claims appended thereto.

REFERENCES

The references which follow are identified by number within the specification. The contents of each of these documents are expressly incorporated herein to the degree necessary to understand the invention.

1. Kotloff, K. L., J. P. Winickoff, B. Ivanoff, J. D. Clemens, D. L. Swerdlow, P. J. Sansonetti, G. K. Adak, and M. M. Levine, *Global burden of Shigella infections: implications for vaccine development and implementation of control strategies*. Bull. WHO, 1999, 77, 651-666.
2. Vahaboglu, H., S. Gundes, A. Karadenizli, B. Mutlu, S. Cetin, F. Kolayli, F. Coskunkan, and V. Dundar, *Transient increase in diarrheal diseases after the devastating earthquake in Kocaeli, Turkey: results of an infectious disease surveillance study*. Clin. Infect. Dis., 2000. 31(6). 1386-1389.
3. Koster, F., J. Levin, L. Walker, K. S. K. Tung, R. H. Gilman, M. M. Rahaman, M. A. Majid, S. Islam, and R. C. Williams, *Hemolytic-uremic syndrome after shigellosis: Relation to endotoxemia and circulating immune complexes*. New England J. Med., 1978, 298(17), 927-933.
4. Talukder, K. A., D. K. Dutta, A. Safa, M. Ansaruzzaman, F. Hassan, K. Alam, K. M. N. Islam, N. I. A. Carlin, G. B. Nair, and D. A. Sack, *Altering Trends in the Dominance of Shigella flexneri Serotypes and Emergence of Serologically Atypical S. flexneri Strains in Dhaka, Bangladesh*. J. lin. Microbiol., 2001. 39(10). 3757-3759.
5. Hoge, C. W., J. M. Gambel, A. Srijan, C. Pitarangsi, and P. Echeverria, *Trends in antibiotic resistance among diarrheal pathogens isolated in Thailand over* 15 *years*. Clin. Infect. Dis., 1998, 26(2), 341-345.
6. Sarkar, K., S. Ghosh, S. K. Niyogi, and S. K. Bhattacharya, *Shigella dysenteriae type* 1 *with reduced susceptibility to fluoroquinolones*. The Lancet, 2003, 361(9359), 785.
7. DuPont, H. L., M. M. Levine, R. B. Hornick, and S. B. Formal, *Inoculum size in shigellosis and implications for expected mode of transmission*. J. Infect. Dis., 1989. 159 (6), 1126-1128.
8. Kolavic, S. A., A. Kimura, S. L. Simons, L. Slutsker, S. Barth, and C. E. Haley, *An outbreak of Shigella dysenteriae type* 2 *among laboratory workers due to intentional food contamination*. JAMA, 1997. 278(5). 396-398.
9. Hedberg, C. W., W. C. Levine, K. E. White, R. H. Carlson, D. K. Winsor, D. N. Cameron, K. L. MacDonald, and M. T. Osterholm, *An international foodborne outbreak of shigellosis associated with a commercial airline*. Jama, 1992, 268(22), 3208-12.
10. Lew, J. F., D. L. Swerdlow, M. E. Dance, P. M. Griffin, C. A. Bopp, M. J. Gillenwater, T. Mercatante, and R. I. Glass, *An outbreak of shigellosis aboard a cruise ship caused by a multiple-antibiotic-resistant strain of Shigella flexneri*. Am J Epidemiol, 1991, 134(4), 413-20.
11. Watarai, M., T. Tobe, M. Yoshikawa, and C. Sasakawa, *Contact of Shigella with host cells triggers release of Ipa invasins and is an essential function of invasiveness*. EMBO J, 1995, 14, 2461-2470.
12. Menard, R., P. Sansonetti, and C. Parsot, *The secretion of the Shigella flexneri Ipa invasins is activated by epithelial cells and controlled by IpaB and IpaD*. EMBO J., 1994, 13(22), 5293-5302.
13. Menard, R., P. J. Sansonetti, and C. Parsot, *Nonpolar mutagenesis of the ipa genes defines IpaB, IpaC, and IpaD as effectors of Shigella flexneri entry into epithelial cells*. J. Bacteriol., 1993, 175, 5899-5906.
14. Sansonetti, P. J., G. T. V. Nhieu, and C. Egile, *Rupture of the intestinal epithelial barrier and mucosal invasion by Shigella flexneri*. Clin. Infect. Dis., 1999, 28, 466-475.
15. Oaks, E. V. and K. R. Turbyfill, *Invaplex from gram negative bacteria, method of purification and methods of use*. 2001: U.S. Pat. No. 6,680,374.
16. Oaks, E. V., K. R. Turbyfill, and A. B. Hartman, *Use of purified invasin complex from gram negative bacteria as a vaccine*. 2001: U.S. Pat. No. 6,277,379.
17. Oaks, E. V. and Turbyfill, K. R. Development and evaluation of a *Shigella flexneri* and *S. sonnei* bivalent invasin complex (Invaplex) vaccine. Vaccine. 2006, 24:2290-2301.
18. Turbyfill, K. R., A. B. Hartman, and E. V. Oaks, *Isolation and characterization of a Shigella flexneri invasin complex subunit vaccine*. Infect. Immun., 2000, 68, 6624-6632.
19. Kaminski, R. W., Turbyfill, K. R. and Oaks, E. V. Mucosal adjuvant properties of the *Shigella* invasin complex. Infect. Immun 2006, 74:2856-2866.
20. Kaminski, R. W., *Immunological and functional characterization of a novel mucosal adjuvant isolated from Shigella* spp. 2004, George Mason University, Fairfax, Va.
21. Noriega, F. R., J. Y. Wang, G. Losonsky, D. R. Maneval, D. M. Hone, and M. M. Levine, *Construction and characterization of attenuated* (*delta*)*aroA* (*delta*)*virG Shigella flexneri* 2*a strain CVD* 1203, *a prototype live oral vaccine*. Infect. Immun., 1994, 62(11), 5168-5172.
22. Sansonefti, P. J., J. Arondel, A. Fontaine, H. d'Hauteville, and M. L. Bernardini, *OmpB* (*osmo-regulation*) *and icsA* (*cell-to-cell spread*) *mutants of Shigella flexneri: vaccine candidates and probes to study the pathogenesis of shigellosis*. Vaccine, 1991, 9(6), 416-422.
23. Chakrabarti, M. K., J. Bhattacharya, M. K. Bhattacharya, G. B. Nair, S. K. Bhattacharya, and D. Mahalanabis, *Killed oral Shigella vaccine made from Shigella flexneri* 2*a protects against challenge in the rabbit model of shigellosis*. Acta Paediatr, 1999, 88(2), 161-5.
24. Mukhopadhaya, A., D. Mahalanabis, J. Khanam, and M. K. Chakrabarti, *Protective efficacy of oral immunization with heat-killed Shigella flexneri* 2*a in animal model: study of cross protection, immune response and antigenic recognition*. Vaccine, 2003, 21(21-22), 3043-50.
25. Orr, N., G. Robin, D. Cohen, R. Arnon, and G. H. Lowell, *Immunogenicity and efficacy of oral or intranasal Shigella flexneri 2a and Shigella sonnei proteosome-lipopolysaccharide vaccines in animal models*. Infect. Immun., 1993, 61(6), 2390-2395.

26. Cohen, D., S. Ashkenazi, M. S. Green, M. Gdalevich, G. Robin, R. Slepon, M. Yavzori, N. Orr, C. Block, I. Ashkenazi, J. Shemer, D. N. Taylor, T. L. Hale, J. C. Sadoff, D. Paviiakova, R. Schneerson, and J. B. Robbins, *Double-blind vaccine-controlled randomised efficacy trial of an investigational Shigella sonnei conjugate vaccine in young adults*. Lancet, 1997, 349, 155-159.

27. Levenson, V. I., T. P. Egorova, Z. P. Belkin, V. G. Fedosova, J. L. Subbotina, E. Z. Rukhadze, E. K. Dzhikidze, and Z. K. Stassilevich, *Protective ribosomal preparation from Shigella sonnei as a parenteral candidate vaccine*. Infect. Immun., 1991, 59(10), 3610-3618.

28. Coster, T. S., C. W. Hoge, L. L. VanDeVerg, A. B. Hartman, E. V. Oaks, M. M. Venkatesan, D. Cohen, G. Robin, A. Fontaine-Thompson, P. J. Sansonetti, and T. L. Hale, *Vaccination against Shigellosis with attenuated Shigella flexneri 2a strain SC602*. Infect. Immun., 1999, 67, 3437-3443.

29. Oaks, E. V., T. L. Hale, and S. B. Formal, *Serum immune response to Shigella protein antigens in Rhesus monkeys and humans infected with Shigella spp*. Infect. Immun., 1986, 53(1). 57-63.

30. Picking, W. L., J. A. Mertz, M. E. Marquart, and W. D. Picking, *Cloning, expression, and affinity purification of recombinant Shigella flexneri invasion plasmid antigens IpaB and IpaC*. Protein Express Purif, 1996, 8, 401-408.

31. Mallett, C. P., L. VanDeVerg, H. H. Collins, and T. L. Hale, *Evaluation of Shigella vaccine safety and efficacy in an intranasally challenged mouse model*. Vaccine, 1993, 11, 190-196.

32. Mills, J. A., J. M. Buysse, and E. V. Oaks, *Shigella flexneri invasion plasmid antigens B and C: Epitope location and characterization with monoclonal antibodies*. Infect. Immun., 1988, 56(11), 2933-2941.

33. Venkatesan, M. M., J. M. Buysse, and D. J. Kopecko, *Characterization of invasion plasmid antigen genes (ipaBCD) from Shigella flexneri*. Proc. Natl. Acad. Sci., USA, 1988, 85, 9317-9321.

34. Harrington, A. T., P. D. Hearn, W. L. Picking, J. R. Barker, A. Wessel, and W. D. Picking, *Structural Characterization of the N Terminus of IpaC from Shigella flexneri*. Infect. Immun., 2003, 71(3), 1255-1264.

35. Page, A., H. Ohayon, P. J. Sansonetti, and C. Parsot, *The secreted IpaB and IpaC invasins and their cytoplasmic chaperone IpgC are required for intercellular dissemination of Shigella flexneri*. Cell Microbiol, 1999, 1, 183-193.

36. Westphal, O. and K. Jann, *Bacterial Lipopolysaccarides. Extraction with Phenolwater and Further Applications of the Procedure*. Methods in Carbohydrate Chemistry, 1965.

37. Venkatesan, M. M., A. B. Hartman, J. W. Newland, V. S. Ivanova, T. L. Hale, M. McDonough, and J. Butterton, *Construction, Characterization, and Animal Testing of WRSd1, a Shigella dysenteriae 1 Vaccine*. Infect. Immun., 2002, 70(6). 2950-2958.

38. Oaks, E. V. and R. W. Kaminski, *Use of Shigella Invaplex to transport functional proteins and transcriptionally-active nucleic acids across mammalian cell membranes in vitro and in vivo*: U.S. Patent application Ser. No. 60/524, 639.

39. Oaks, E. V., M. E. Wingfield, and S. B. Formal, *Plaque formation by virulent Shigella flexneri*. Infect. Immun., 1985, 48(1), 124-129.

40. Hale, T. L. and P. F. Bonventre, *Shigella infection of Henle intestinal epithelial cells: Role of the bacterium*. Infect. Immun., 1979, 24(3), 879-886.

41. Hale, T. L., R. E. Morris, and P. F. Bonventre, *Shigella infection of Henle intestinal epithelial cells: Role of the host cell*. Infect. Immun., 1979, 24(3), 887-894.

42. Davis, R., M. E. Marquart, D. Lucius, and W. D. Picking, *Protein-protein interactions in the assembly of Shigella flexneri invasion plasmid antigens IpaB and IpaC into protein complexes*. Biochem. Biophys. Acta, 1998, 1429, 45-56.

43. Karkhanis, Y., J. Zeltner, J. Jackson, and D. Carlo, *A new and improved microassay to determine 2-keto-3-deoxyoctonate in lipopolysaccharide of Gram-negative bacteria*. Anal Biochem, 1978, 85(2), 595-601.

44. Hartman, A. B., C. J. Powell, C. L. Shulta, E. V. Oaks, and K. H. Eckels, *Small-animal model to measure efficacy and immunogenicity of Shigella vaccine strains*. Infec. Immun., 1991, 59(11), 4075-4083.

45. Hartman, A. B., L.v.d. Verg, H. H. Collins, D. B. Tang, N. O. Benduik, D. N. Taylor, and C. J. Powell, *Local immune response and protection in the guinea pig keratoconjunctivitis model following immunization with Shigella vaccines*. Infect. Immun., 1994, 62, 412-420.

46. Turbyfill, K. R., J. A. Mertz, C. P. Mallett, and E. V. Oaks, *Identification of epitope and surface-exposed domains of Shigella flexneri Invasion Plasmid Antigen D (IpaD)*. Infect. Immun., 1998, 66, 1999-2006.

47. Belec, L., D. Meillet, O. Gaillard, T. Prazuck, E. Michel, J. N. Ekome, and J. Pillot, *Decreased cervicovaginal production of both IgA1 and IgA2 subclasses in women with AIDS*. Clin. Exp. Immunol., 1995, 101, 100-106.

48. Malich, G., *The sensitivity and specificity of the MTS tetrazolium assay for detecting the in vitro cytotoxicity of 20 chemicals using human cell lines*. Toxicology, 1997, 124(3), 179-192.

49. Hale, T. L., *Genetic basis of virulence in Shigella species*. Microbiol. Rev., 1991, 55(2), 206-224.

50. Mallett, C. P., T. L. Hale, R. W. Kaminski, T. Larsen, N. Orr, D. Cohen, and G. H. Lowell, *Intranasal or intragastric immunization with proteosome-Shigella lipopolysaccharide vaccines protects against lethal pneumonia in a murine model of Shigella infection*. Infect. Immun., 1995, 63, 2382-2386.

51. Levenson, V. J., C. P. Mallett, and T. L. Hale, *Protection against local Shigella sonnei infection in mice by parenteral immunization with a nucleoprotein subcellular vaccine*. Infect. Immun., 1995, 63, 2762-2765.

52. van de Verg, L., C. Mallett, H. Collins, T. Larsen, C. Hammack, and T. Hale, *Antibody and cytokine responses in a mouse pulmonary model of Shigella flexneri serotype 2a infection*. Infect. Immun., 1995, 63(5), 1947-1954.

53. Alexander, W. A., A. B. Hartman, E. V. Oaks, and M. M. Venkatesan, *Construction and characterization of virG (icsA)—deleted Escherichia coli K12-Shigella flexneri hybrid vaccine strains*. Vaccine, 1996, 14(11), 1053-61.

54. Hartman, A. B. and M. M. Venkatesan, *Construction of a stable attenuated Shigella sonnei deltavirG vaccine strain, WRSS 1, and protective efficacy and immunogenicity in the guinea pig keratoconjunctivitis model*. Infect. Immun., 1998, 66, 4572-4576.

55. Linde, K., V. Dentchev, V. Bonkarenko, S. Marinova, B. Randhagen, M. Bratoyeve, Y. Tsvetanov, and Y. Romanova, *Live Shigella flexneri 2a and Shigella sonnei I vaccine candidate strains with two attenuating markers. I. Construction of vaccine candidate strains with retained invasiveness but reduced intracellular multiplication*. Vaccine, 1990, 8, 25-29.

56. Verma, N. K. and A. A. Lindberg, *Construction of aromatic dependent Shigella flexneri 2a live vaccine candidate strains:deletion mutations in the aroA and aroD genes*. Vaccine, 1991, 9, 6-9.

What is claimed:

1. An artificial Invaplex consisting of IpaB:IpaC complex complexed with a purified lipopolysaccharide (LPS) from a gram negative bacteria selected from *S. flexneri, S. sonnei, S. dysenteriae, S. boydii, enteroinvasive E. coli, Yersinia or Salmonella*, wherein the artificial Invaplex is prepared by mixing IpaB and IpaC to form a complex, IpaB:IpaC, and then mixing IpaB:IpaC with the lipopolysaccharide to form the artificial Invaplex and wherein the IpaB and the IpaC are recombinantly produced and of *Shigella* origin.

2. The artificial Invaplex of claim 1, wherein the lipopolysaccharide is from a gram negative bacteria selected from *S. flexneri, S. sonnei, S. dysenteriae, S. boydii*, or enteroinvasive *E. coli*.

3. The artificial Invaplex of claim 2, wherein the lipopolysaccharide is from a gram negative bacteria selected from *S. flexneri, S. sonnei, S. boydii, or S. dysenteriae*.

4. The artificial Invaplex of claim 1, wherein the LPS is from a *Shigella* serotype.

5. The artificial Invaplex of claim 1, wherein the IpaB is purified recombinant IpaB.

6. The artificial Invaplex of claim 1, wherein the IpaC is purified recombinant IpaC.

7. The artificial Invaplex of claim 1, wherein the IpaC, IpaB and lipopolysaccharide are present in amounts that correspond to those of native Invaplex 24.

8. The artificial Invaplex of claim 1, wherein the lipopolysaccharide includes two or more lipopolysaccharides selected from at least two different serotypes of gram negative bacteria.

9. The artificial Invaplex of claim 1, wherein the IpaC and IpaB are present in an IpaC:IpaB ratio in the range of 0.08:1 to 80:1.

10. The artificial Invaplex of claim 9, wherein the IpaC:IpaB ratio is 0.8:1 to 20:1.

11. The artificial Invaplex of claim 10, wherein the IpaC:IpaB ratio is approximately 8:1.

12. The artificial Invaplex of claim 1, wherein the LPS is present relative to the total protein (IpaB and IpaC) in an LPS:protein ratio selected from the range of 0.01:1 to 10:1.

13. The artificial Invaplex of claim 12, wherein the LPS:protein ratio range is from 0.5:1 to 5:1.

14. The artificial Invaplex of claim 13, wherein the LPS:protein ratio is approximately 0.5:1.

15. The artificial Invaplex of claim 1, further comprising a labeled detectant, antibiotic, therapeutic or biomolecule.

16. The artificial Invaplex of claim 15, wherein the biomolecule includes proteins, enzymes, polysaccharide, or nucleic acids.

17. A composition comprising the artificial Invaplex of claim 1 and a pharmaceutically acceptable carrier.

18. The composition of claim 17 further comprising an immunogen.

19. The composition of claim 17, wherein the artificial Invaplex present is sufficient to enhance an immune response to an immunogen.

20. The composition of claim 17, wherein the amount of artificial Invaplex present is sufficient to induce a protective immune response.

21. The composition of claim 17, wherein the artificial Invaplex further comprises a labeled detectant, antibiotic, therapeutic or biomolecule.

22. The composition of claim 21, wherein the biomolecule includes proteins, enzymes, polysaccharide or nucleic acids.

23. The composition comprising the artificial Invaplex of claim 8 and a pharmaceutically acceptable carrier.

* * * * *